US010058606B2

(12) United States Patent
Wu et al.

(10) Patent No.: US 10,058,606 B2
(45) Date of Patent: Aug. 28, 2018

(54) HEPATITIS B THERAPEUTIC VACCINES

(71) Applicant: TheVax Genetics Vaccine Co., Ltd., Taipei (TW)

(72) Inventors: Chia-Mao Wu, Hsinchu County (TW); Jiun-Ming Wu, Hsinchu County (TW); Yi-Chia Lin, Hsinchu County (TW); Kung-Lung Lee, Hsinchu County (TW); Chia-Hao Kang, Hsinchu County (TW); Fu-Hsien Chiang, Hsinchu County (TW); Cheng-Yung Chang, Hsinchu County (TW); Wei-Lun Chang, Hsinchu County (TW); Hsiang-Kai Lin, Hsinchu County (TW); Chia-Kuan Peng, Hsinchu County (TW); Wei-Hsiang Lin, Hsinchu County (TW); Yi-Tsui Chiu, Hsinchu County (TW)

(73) Assignee: TheVax Genetics Vaccine Co., Ltd., Taipei (TW)

( * ) Notice: Subject to any disclaimer, the term of this patent is extended or adjusted under 35 U.S.C. 154(b) by 0 days.

(21) Appl. No.: 15/701,352

(22) Filed: Sep. 11, 2017

(65) Prior Publication Data

US 2018/0078636 A1 Mar. 22, 2018

Related U.S. Application Data

(60) Provisional application No. 62/396,642, filed on Sep. 19, 2016.

(51) Int. Cl.

| | |
|---|---|
| ***A61K 39/00*** | (2006.01) |
| ***A61K 39/385*** | (2006.01) |
| ***A61K 39/12*** | (2006.01) |
| ***C07K 14/005*** | (2006.01) |
| ***C07K 14/21*** | (2006.01) |
| ***A61K 39/29*** | (2006.01) |
| ***C12N 7/00*** | (2006.01) |

(52) U.S. Cl.

CPC .......... *A61K 39/292* (2013.01); *C07K 14/005* (2013.01); *C12N 7/00* (2013.01); *A61K 2039/55561* (2013.01); *A61K 2039/57* (2013.01); *A61K 2039/575* (2013.01); *C07K 2319/02* (2013.01); *C07K 2319/04* (2013.01); *C07K 2319/10* (2013.01); *C07K 2319/40* (2013.01); *C07K 2319/74* (2013.01); *C12N 2730/10122* (2013.01); *C12N 2730/10134* (2013.01); *C12N 2730/10171* (2013.01)

(58) Field of Classification Search

CPC .............. A61K 2300/00; A61K 31/135; A61K 31/196; A61K 31/277; A61K 31/353

See application file for complete search history.

(56) References Cited

U.S. PATENT DOCUMENTS

| | | | |
|---|---|---|---|
| 8,846,080 | B2 | 9/2014 | Biemans et al. |
| 2014/0154280 | A1 | 6/2014 | Chou et al. |
| 2014/0154285 | A1 | 6/2014 | Wu et al. |

*Primary Examiner* — Barry A Chestnut

(74) *Attorney, Agent, or Firm* — Hsiu-Ming Saunders; Intellectual Property Connections, Inc.

(57) ABSTRACT

A fusion protein for use as a hepatitis B therapeutic vaccine is disclosed. The fusion protein comprises: (a) an antigen-presenting cell (APC)-binding domain or a CD91 receptor-binding domain; (b) a protein transduction domain; and (c) an antigen comprising a hepatitis B virus X protein deletion mutant that lacks amino acids (aa) at least from as 21 to as 50. The protein transduction domain is a fusion polypeptide comprising a T cell sensitizing signal-transducing peptide, a linker, and a translocation peptide. The APC-binding domain or the CD91 receptor-binding domain is located at the N-terminus of the fusion protein, and the antigen is located at the C-terminus of the protein transduction domain.

20 Claims, 4 Drawing Sheets

Specification includes a Sequence Listing.

SEQUENCE LISTING

```
<160> NUMBER OF SEQ ID NOS: 34

<210> SEQ ID NO 1
<211> LENGTH: 28
<212> TYPE: PRT
<213> ORGANISM: Homo sapiens

<400> SEQUENCE: 1
```

```
Thr Asp Ile Tyr Phe Cys Lys Ile Glu Val Met Tyr Pro Pro Pro Tyr
1               5                   10                  15

Leu Asp Asn Glu Lys Ser Asn Gly Thr Ile Ile His
            20                  25


<210> SEQ ID NO 2
<211> LENGTH: 53
<212> TYPE: PRT
<213> ORGANISM: Homo sapiens

<400> SEQUENCE: 2

Asn Cys Asp Gly Lys Leu Gly Asn Glu Ser Val Thr Phe Tyr Leu Gln
1               5                   10                  15

Asn Leu Tyr Val Asn Gln Thr Asp Ile Tyr Phe Cys Lys Ile Glu Val
            20                  25                  30

Met Tyr Pro Pro Pro Tyr Leu Asp Asn Glu Lys Ser Asn Gly Thr Ile
        35                  40                  45

Ile His Val Lys Gly
    50


<210> SEQ ID NO 3
<211> LENGTH: 34
<212> TYPE: PRT
<213> ORGANISM: Pseudomonas aeruginosa

<400> SEQUENCE: 3

Gly Trp Glu Gln Leu Glu Gln Cys Gly Tyr Pro Val Gln Arg Leu Val
1               5                   10                  15

Ala Leu Tyr Leu Ala Ala Arg Leu Ser Trp Asn Gln Val Asp Gln Val
            20                  25                  30

Ile Arg


<210> SEQ ID NO 4
<211> LENGTH: 112
<212> TYPE: PRT
<213> ORGANISM: Pseudomonas aeruginosa

<400> SEQUENCE: 4

Gly Gly Ser Leu Ala Ala Leu Thr Ala His Gln Ala Cys His Leu Pro
1               5                   10                  15

Leu Glu Thr Phe Thr Arg His Arg Gln Pro Arg Gly Trp Glu Gln Leu
            20                  25                  30

Glu Gln Cys Gly Tyr Pro Val Gln Arg Leu Val Ala Leu Tyr Leu Ala
        35                  40                  45

Ala Arg Leu Ser Trp Asn Gln Val Asp Gln Val Ile Arg Asn Ala Leu
    50                  55                  60

Ala Ser Pro Gly Ser Gly Gly Asp Leu Gly Glu Ala Ile Arg Glu Gln
65                  70                  75                  80

Pro Glu Gln Ala Arg Leu Ala Leu Thr Leu Ala Ala Ala Glu Ser Glu
                85                  90                  95

Arg Phe Val Arg Gln Gly Thr Gly Asn Asp Glu Ala Gly Ala Ala Asn
            100                 105                 110


<210> SEQ ID NO 5
<211> LENGTH: 104
<212> TYPE: PRT
<213> ORGANISM: Homo sapiens

<400> SEQUENCE: 5
```

```
Ala Glu Phe Glu Glu Pro Arg Val Ile Asp Leu Trp Asp Leu Ala Gln
1               5                   10                  15

Ser Ala Asn Leu Thr Asp Lys Glu Leu Glu Ala Phe Arg Glu Glu Leu
            20                  25                  30

Lys His Phe Glu Ala Lys Ile Glu Lys His Asn His Tyr Gln Lys Gln
        35                  40                  45

Leu Glu Ile Ala His Glu Lys Leu Arg His Ala Glu Ser Val Gly Asp
    50                  55                  60

Gly Glu Arg Val Ser Arg Ser Arg Glu Lys His Ala Leu Leu Glu Gly
65                  70                  75                  80

Arg Thr Lys Glu Leu Gly Tyr Thr Val Lys Lys His Leu Gln Asp Leu
                85                  90                  95

Ser Gly Arg Ile Ser Arg Ala Arg
            100
```

<210> SEQ ID NO 6
<211> LENGTH: 153
<212> TYPE: PRT
<213> ORGANISM: Homo sapiens

<400> SEQUENCE: 6

```
Val Tyr Leu Gln Thr Ser Leu Lys Tyr Asn Ile Leu Pro Glu Lys Glu
1               5                   10                  15

Glu Phe Pro Phe Ala Leu Gly Val Gln Thr Leu Pro Gln Thr Cys Asp
            20                  25                  30

Glu Pro Lys Ala His Thr Ser Phe Gln Ile Ser Leu Ser Val Ser Tyr
        35                  40                  45

Thr Gly Ser Arg Ser Ala Ser Asn Met Ala Ile Val Asp Val Lys Met
    50                  55                  60

Val Ser Gly Phe Ile Pro Leu Lys Pro Thr Val Lys Met Leu Glu Arg
65                  70                  75                  80

Ser Asn His Val Ser Arg Thr Glu Val Ser Ser Asn His Val Leu Ile
                85                  90                  95

Tyr Leu Asp Lys Val Ser Asn Gln Thr Leu Ser Leu Phe Phe Thr Val
            100                 105                 110

Leu Gln Asp Val Pro Val Arg Asp Leu Lys Pro Ala Ile Val Lys Val
        115                 120                 125

Tyr Asp Tyr Tyr Glu Thr Asp Glu Phe Ala Ile Ala Glu Tyr Asn Ala
    130                 135                 140

Pro Cys Ser Lys Asp Leu Gly Asn Ala
145                 150
```

<210> SEQ ID NO 7
<211> LENGTH: 24
<212> TYPE: PRT
<213> ORGANISM: Human immunodeficiency virus

<400> SEQUENCE: 7

```
Arg Gly Asp Pro Thr Gly Gln Glu Glu Ser Lys Glu Lys Val Glu Lys
1               5                   10                  15

Glu Thr Val Val Asp Pro Val Thr
            20
```

<210> SEQ ID NO 8
<211> LENGTH: 641
<212> TYPE: PRT
<213> ORGANISM: Homo sapiens

<400> SEQUENCE: 8

Met Ala Lys Ala Ala Ala Ile Gly Ile Asp Leu Gly Thr Thr Tyr Ser
1               5                   10                  15

Cys Val Gly Val Phe Gln His Gly Lys Val Glu Ile Ile Ala Asn Asp
            20                  25                  30

Gln Gly Asn Arg Thr Thr Pro Ser Tyr Val Ala Phe Thr Asp Thr Glu
        35                  40                  45

Arg Leu Ile Gly Asp Ala Ala Lys Asn Gln Val Ala Leu Asn Pro Gln
    50                  55                  60

Asn Thr Val Phe Asp Ala Lys Arg Leu Ile Gly Arg Lys Phe Gly Asp
65                  70                  75                  80

Pro Val Val Gln Ser Asp Met Lys His Trp Pro Phe Gln Val Ile Asn
                85                  90                  95

Asp Gly Asp Lys Pro Lys Val Gln Val Ser Tyr Lys Gly Glu Thr Lys
            100                 105                 110

Ala Phe Tyr Pro Glu Glu Ile Ser Ser Met Val Leu Thr Lys Met Lys
        115                 120                 125

Glu Ile Ala Glu Ala Tyr Leu Gly Tyr Pro Val Thr Asn Ala Val Ile
    130                 135                 140

Thr Val Pro Ala Tyr Phe Asn Asp Ser Gln Arg Gln Ala Thr Lys Asp
145                 150                 155                 160

Ala Gly Val Ile Ala Gly Leu Asn Val Leu Arg Ile Ile Asn Glu Pro
                165                 170                 175

Thr Ala Ala Ala Ile Ala Tyr Gly Leu Asp Arg Thr Gly Lys Gly Glu
            180                 185                 190

Arg Asn Val Leu Ile Phe Asp Leu Gly Gly Gly Thr Phe Asp Val Ser
        195                 200                 205

Ile Leu Thr Ile Asp Asp Gly Ile Phe Glu Val Lys Ala Thr Ala Gly
    210                 215                 220

Asp Thr His Leu Gly Gly Glu Asp Phe Asp Asn Arg Leu Val Asn His
225                 230                 235                 240

Phe Val Glu Glu Phe Lys Arg Lys His Lys Lys Asp Ile Ser Gln Asn
                245                 250                 255

Lys Arg Ala Val Arg Arg Leu Arg Thr Ala Cys Glu Arg Ala Lys Arg
            260                 265                 270

Thr Leu Ser Ser Ser Thr Gln Ala Ser Leu Glu Ile Asp Ser Leu Phe
        275                 280                 285

Glu Gly Ile Asp Phe Tyr Thr Ser Ile Thr Arg Ala Arg Phe Glu Glu
    290                 295                 300

Leu Cys Ser Asp Leu Phe Arg Ser Thr Leu Glu Pro Val Glu Lys Ala
305                 310                 315                 320

Leu Arg Asp Ala Lys Leu Asp Lys Ala Gln Ile His Asp Leu Val Leu
                325                 330                 335

Val Gly Gly Ser Thr Arg Ile Pro Lys Val Gln Lys Leu Leu Gln Asp
            340                 345                 350

Phe Phe Asn Gly Arg Asp Leu Asn Lys Ser Ile Asn Pro Asp Glu Ala
        355                 360                 365

Val Ala Tyr Gly Ala Ala Val Gln Ala Ala Ile Leu Met Gly Asp Lys
    370                 375                 380

Ser Glu Asn Val Gln Asp Leu Leu Leu Leu Asp Val Ala Pro Leu Ser
385                 390                 395                 400

Leu Gly Leu Glu Thr Ala Gly Gly Val Met Thr Ala Leu Ile Lys Arg

-continued

```
                405                 410                 415

Asn Ser Thr Ile Pro Thr Lys Gln Thr Gln Ile Phe Thr Thr Tyr Ser
            420                 425                 430

Asp Asn Gln Pro Gly Val Leu Ile Gln Val Tyr Glu Gly Glu Arg Ala
        435                 440                 445

Met Thr Lys Asp Asn Asn Leu Leu Gly Arg Phe Glu Leu Ser Gly Ile
    450                 455                 460

Pro Pro Ala Pro Arg Gly Val Pro Gln Ile Glu Val Thr Phe Asp Ile
465                 470                 475                 480

Asp Ala Asn Gly Ile Leu Asn Val Thr Ala Thr Asp Lys Ser Thr Gly
                485                 490                 495

Lys Ala Asn Lys Ile Thr Ile Thr Asn Asp Lys Gly Arg Leu Ser Lys
            500                 505                 510

Glu Glu Ile Glu Arg Met Val Gln Glu Ala Glu Lys Tyr Lys Ala Glu
        515                 520                 525

Asp Glu Val Gln Arg Glu Arg Val Ser Ala Lys Asn Ala Leu Glu Ser
    530                 535                 540

Tyr Ala Phe Asn Met Lys Ser Ala Val Glu Asp Glu Gly Leu Lys Gly
545                 550                 555                 560

Lys Ile Ser Glu Ala Asp Lys Lys Lys Val Leu Asp Lys Cys Gln Glu
                565                 570                 575

Val Ile Ser Trp Leu Asp Ala Asn Thr Leu Ala Glu Lys Asp Glu Phe
            580                 585                 590

Glu His Lys Arg Lys Glu Leu Glu Gln Val Cys Asn Pro Ile Ile Ser
        595                 600                 605

Gly Leu Tyr Gln Gly Ala Gly Gly Pro Gly Pro Gly Gly Phe Gly Ala
    610                 615                 620

Gln Gly Pro Lys Gly Gly Ser Gly Ser Gly Pro Thr Ile Glu Glu Val
625                 630                 635                 640

Asp


<210> SEQ ID NO 9
<211> LENGTH: 252
<212> TYPE: PRT
<213> ORGANISM: Pseudomonas aeruginosa

<400> SEQUENCE: 9

Ala Glu Glu Ala Phe Asp Leu Trp Asn Glu Cys Ala Lys Ala Cys Val
1               5                   10                  15

Leu Asp Leu Lys Asp Gly Val Arg Ser Ser Arg Met Ser Val Asp Pro
            20                  25                  30

Ala Ile Ala Asp Thr Asn Gly Gln Gly Val Leu His Tyr Ser Met Val
        35                  40                  45

Leu Glu Gly Gly Asn Asp Ala Leu Lys Leu Ala Ile Asp Asn Ala Leu
    50                  55                  60

Ser Ile Thr Ser Asp Gly Leu Thr Ile Arg Leu Glu Gly Gly Val Glu
65                  70                  75                  80

Pro Asn Lys Pro Val Arg Tyr Ser Tyr Thr Arg Gln Ala Arg Gly Ser
                85                  90                  95

Trp Ser Leu Asn Trp Leu Val Pro Ile Gly His Glu Lys Pro Ser Asn
            100                 105                 110

Ile Lys Val Phe Ile His Glu Leu Asn Ala Gly Asn Gln Leu Ser His
        115                 120                 125

Met Ser Pro Ile Tyr Thr Ile Glu Met Gly Asp Glu Leu Leu Ala Lys
```

-continued

```
    130                 135                 140

Leu Ala Arg Asp Ala Thr Phe Phe Val Arg Ala His Glu Ser Asn Glu
145                 150                 155                 160

Met Gln Pro Thr Leu Ala Ile Ser His Ala Gly Val Ser Val Val Met
                165                 170                 175

Ala Gln Thr Gln Pro Arg Arg Glu Lys Arg Trp Ser Glu Trp Ala Ser
            180                 185                 190

Gly Lys Val Leu Cys Leu Leu Asp Pro Leu Asp Gly Val Tyr Asn Tyr
        195                 200                 205

Leu Ala Gln Gln Arg Cys Asn Leu Asp Asp Thr Trp Glu Gly Lys Ile
    210                 215                 220

Tyr Arg Val Leu Ala Gly Asn Pro Ala Lys His Asp Leu Asp Ile Lys
225                 230                 235                 240

Pro Thr Val Ile Ser His Arg Leu His Phe Pro Glu
                245                 250


<210> SEQ ID NO 10
<211> LENGTH: 613
<212> TYPE: PRT
<213> ORGANISM: Pseudomonas aeruginosa

<400> SEQUENCE: 10

Ala Glu Glu Ala Phe Asp Leu Trp Asn Glu Cys Ala Lys Ala Cys Val
1               5                   10                  15

Leu Asp Leu Lys Asp Gly Val Arg Ser Ser Arg Met Ser Val Asp Pro
            20                  25                  30

Ala Ile Ala Asp Thr Asn Gly Gln Gly Val Leu His Tyr Ser Met Val
        35                  40                  45

Leu Glu Gly Gly Asn Asp Ala Leu Lys Leu Ala Ile Asp Asn Ala Leu
    50                  55                  60

Ser Ile Thr Ser Asp Gly Leu Thr Ile Arg Leu Glu Gly Gly Val Glu
65                  70                  75                  80

Pro Asn Lys Pro Val Arg Tyr Ser Tyr Thr Arg Gln Ala Arg Gly Ser
                85                  90                  95

Trp Ser Leu Asn Trp Leu Val Pro Ile Gly His Glu Lys Pro Ser Asn
            100                 105                 110

Ile Lys Val Phe Ile His Glu Leu Asn Ala Gly Asn Gln Leu Ser His
        115                 120                 125

Met Ser Pro Ile Tyr Thr Ile Glu Met Gly Asp Glu Leu Leu Ala Lys
    130                 135                 140

Leu Ala Arg Asp Ala Thr Phe Phe Val Arg Ala His Glu Ser Asn Glu
145                 150                 155                 160

Met Gln Pro Thr Leu Ala Ile Ser His Ala Gly Val Ser Val Val Met
                165                 170                 175

Ala Gln Thr Gln Pro Arg Arg Glu Lys Arg Trp Ser Glu Trp Ala Ser
            180                 185                 190

Gly Lys Val Leu Cys Leu Leu Asp Pro Leu Asp Gly Val Tyr Asn Tyr
        195                 200                 205

Leu Ala Gln Gln Arg Cys Asn Leu Asp Asp Thr Trp Glu Gly Lys Ile
    210                 215                 220

Tyr Arg Val Leu Ala Gly Asn Pro Ala Lys His Asp Leu Asp Ile Lys
225                 230                 235                 240

Pro Thr Val Ile Ser His Arg Leu His Phe Pro Glu Gly Gly Ser Leu
                245                 250                 255
```

```
Ala Ala Leu Thr Ala His Gln Ala Cys His Leu Pro Leu Glu Thr Phe
            260                 265                 270

Thr Arg His Arg Gln Pro Arg Gly Trp Glu Gln Leu Glu Gln Cys Gly
        275                 280                 285

Tyr Pro Val Gln Arg Leu Val Ala Leu Tyr Leu Ala Ala Arg Leu Ser
    290                 295                 300

Trp Asn Gln Val Asp Gln Val Ile Arg Asn Ala Leu Ala Ser Pro Gly
305                 310                 315                 320

Ser Gly Gly Asp Leu Gly Glu Ala Ile Arg Glu Gln Pro Glu Gln Ala
                325                 330                 335

Arg Leu Ala Leu Thr Leu Ala Ala Ala Glu Ser Glu Arg Phe Val Arg
            340                 345                 350

Gln Gly Thr Gly Asn Asp Glu Ala Gly Ala Ala Asn Ala Asp Val Val
        355                 360                 365

Ser Leu Thr Cys Pro Val Ala Ala Gly Glu Cys Ala Gly Pro Ala Asp
    370                 375                 380

Ser Gly Asp Ala Leu Leu Glu Arg Asn Tyr Pro Thr Gly Ala Glu Phe
385                 390                 395                 400

Leu Gly Asp Gly Gly Asp Val Ser Phe Ser Thr Arg Gly Thr Gln Asn
                405                 410                 415

Trp Thr Val Glu Arg Leu Leu Gln Ala His Arg Gln Leu Glu Glu Arg
            420                 425                 430

Gly Tyr Val Phe Val Gly Tyr His Gly Thr Phe Leu Glu Ala Ala Gln
        435                 440                 445

Ser Ile Val Phe Gly Gly Val Arg Ala Arg Ser Gln Asp Leu Asp Ala
    450                 455                 460

Ile Trp Arg Gly Phe Tyr Ile Ala Gly Asp Pro Ala Leu Ala Tyr Gly
465                 470                 475                 480

Tyr Ala Gln Asp Gln Glu Pro Asp Ala Arg Gly Arg Ile Arg Asn Gly
                485                 490                 495

Ala Leu Leu Arg Val Tyr Val Pro Arg Ser Ser Leu Pro Gly Phe Tyr
            500                 505                 510

Arg Thr Ser Leu Thr Leu Ala Ala Pro Glu Ala Ala Gly Glu Val Glu
        515                 520                 525

Arg Leu Ile Gly His Pro Leu Pro Leu Arg Leu Asp Ala Ile Thr Gly
    530                 535                 540

Pro Glu Glu Glu Gly Gly Arg Leu Glu Thr Ile Leu Gly Trp Pro Leu
545                 550                 555                 560

Ala Glu Arg Thr Val Val Ile Pro Ser Ala Ile Pro Thr Asp Pro Arg
                565                 570                 575

Asn Val Gly Gly Asp Leu Asp Pro Ser Ser Ile Pro Asp Lys Glu Gln
            580                 585                 590

Ala Ile Ser Ala Leu Pro Asp Tyr Ala Ser Gln Pro Gly Lys Pro Pro
        595                 600                 605

Arg Glu Asp Leu Lys
    610


<210> SEQ ID NO 11
<211> LENGTH: 323
<212> TYPE: PRT
<213> ORGANISM: Homo sapiens

<400> SEQUENCE: 11

Tyr Ser Arg Glu Lys Asn Gln Pro Lys Pro Ser Pro Lys Arg Glu Ser
1               5                   10                  15
```

```
Gly Glu Glu Phe Arg Met Glu Lys Leu Asn Gln Leu Trp Glu Lys Ala
            20                  25                  30

Gln Arg Leu His Leu Pro Pro Val Arg Leu Ala Glu Leu His Ala Asp
        35                  40                  45

Leu Lys Ile Gln Glu Arg Asp Glu Leu Ala Trp Lys Lys Leu Lys Leu
    50                  55                  60

Asp Gly Leu Asp Glu Asp Gly Glu Lys Glu Ala Arg Leu Ile Arg Asn
65                  70                  75                  80

Leu Asn Val Ile Leu Ala Lys Tyr Gly Leu Asp Gly Lys Lys Asp Ala
                85                  90                  95

Arg Gln Val Thr Ser Asn Ser Leu Ser Gly Thr Gln Glu Asp Gly Leu
            100                 105                 110

Asp Asp Pro Arg Leu Glu Lys Leu Trp His Lys Ala Lys Thr Ser Gly
        115                 120                 125

Lys Phe Ser Gly Glu Glu Leu Asp Lys Leu Trp Arg Glu Phe Leu His
    130                 135                 140

His Lys Glu Lys Val His Glu Tyr Asn Val Leu Leu Glu Thr Leu Ser
145                 150                 155                 160

Arg Thr Glu Glu Ile His Glu Asn Val Ile Ser Pro Ser Asp Leu Ser
                165                 170                 175

Asp Ile Lys Gly Ser Val Leu His Ser Arg His Thr Glu Leu Lys Glu
            180                 185                 190

Lys Leu Arg Ser Ile Asn Gln Gly Leu Asp Arg Leu Arg Arg Val Ser
        195                 200                 205

His Gln Gly Tyr Ser Thr Glu Ala Glu Phe Glu Glu Pro Arg Val Ile
    210                 215                 220

Asp Leu Trp Asp Leu Ala Gln Ser Ala Asn Leu Thr Asp Lys Glu Leu
225                 230                 235                 240

Glu Ala Phe Arg Glu Glu Leu Lys His Phe Glu Ala Lys Ile Glu Lys
                245                 250                 255

His Asn His Tyr Gln Lys Gln Leu Glu Ile Ala His Glu Lys Leu Arg
            260                 265                 270

His Ala Glu Ser Val Gly Asp Gly Glu Arg Val Ser Arg Ser Arg Glu
        275                 280                 285

Lys His Ala Leu Leu Glu Gly Arg Thr Lys Glu Leu Gly Tyr Thr Val
    290                 295                 300

Lys Lys His Leu Gln Asp Leu Ser Gly Arg Ile Ser Arg Ala Arg His
305                 310                 315                 320

Asn Glu Leu


<210> SEQ ID NO 12
<211> LENGTH: 357
<212> TYPE: PRT
<213> ORGANISM: Homo sapiens

<400> SEQUENCE: 12

Met Ala Pro Arg Arg Val Arg Ser Phe Leu Arg Gly Leu Pro Ala Leu
1               5                   10                  15

Leu Leu Leu Leu Leu Phe Leu Gly Pro Trp Pro Ala Ala Ser His Gly
            20                  25                  30

Gly Lys Tyr Ser Arg Glu Lys Asn Gln Pro Lys Pro Ser Pro Lys Arg
        35                  40                  45

Glu Ser Gly Glu Glu Phe Arg Met Glu Lys Leu Asn Gln Leu Trp Glu
    50                  55                  60
```

```
Lys Ala Gln Arg Leu His Leu Pro Pro Val Arg Leu Ala Glu Leu His
65                  70                  75                  80

Ala Asp Leu Lys Ile Gln Glu Arg Asp Glu Leu Ala Trp Lys Lys Leu
                85                  90                  95

Lys Leu Asp Gly Leu Asp Glu Asp Gly Glu Lys Glu Ala Arg Leu Ile
            100                 105                 110

Arg Asn Leu Asn Val Ile Leu Ala Lys Tyr Gly Leu Asp Gly Lys Lys
        115                 120                 125

Asp Ala Arg Gln Val Thr Ser Asn Ser Leu Ser Gly Thr Gln Glu Asp
    130                 135                 140

Gly Leu Asp Asp Pro Arg Leu Glu Lys Leu Trp His Lys Ala Lys Thr
145                 150                 155                 160

Ser Gly Lys Phe Ser Gly Glu Glu Leu Asp Lys Leu Trp Arg Glu Phe
                165                 170                 175

Leu His His Lys Glu Lys Val His Glu Tyr Asn Val Leu Leu Glu Thr
            180                 185                 190

Leu Ser Arg Thr Glu Glu Ile His Glu Asn Val Ile Ser Pro Ser Asp
        195                 200                 205

Leu Ser Asp Ile Lys Gly Ser Val Leu His Ser Arg His Thr Glu Leu
    210                 215                 220

Lys Glu Lys Leu Arg Ser Ile Asn Gln Gly Leu Asp Arg Leu Arg Arg
225                 230                 235                 240

Val Ser His Gln Gly Tyr Ser Thr Glu Ala Glu Phe Glu Glu Pro Arg
                245                 250                 255

Val Ile Asp Leu Trp Asp Leu Ala Gln Ser Ala Asn Leu Thr Asp Lys
            260                 265                 270

Glu Leu Glu Ala Phe Arg Glu Glu Leu Lys His Phe Glu Ala Lys Ile
        275                 280                 285

Glu Lys His Asn His Tyr Gln Lys Gln Leu Glu Ile Ala His Glu Lys
    290                 295                 300

Leu Arg His Ala Glu Ser Val Gly Asp Gly Glu Arg Val Ser Arg Ser
305                 310                 315                 320

Arg Glu Lys His Ala Leu Leu Glu Gly Arg Thr Lys Glu Leu Gly Tyr
                325                 330                 335

Thr Val Lys Lys His Leu Gln Asp Leu Ser Gly Arg Ile Ser Arg Ala
            340                 345                 350

Arg His Asn Glu Leu
        355
```

<210> SEQ ID NO 13
<211> LENGTH: 101
<212> TYPE: PRT
<213> ORGANISM: Human immunodeficiency virus

<400> SEQUENCE: 13

```
Met Glu Pro Val Asp Pro Arg Leu Glu Pro Trp Lys His Pro Gly Ser
1               5                   10                  15

Gln Pro Lys Thr Pro Cys Thr Lys Cys Tyr Cys Lys Lys Cys Cys Leu
            20                  25                  30

His Cys Gln Val Cys Phe Met Thr Lys Gly Leu Gly Ile Ser Tyr Gly
        35                  40                  45

Arg Lys Lys Arg Arg Gln Arg Arg Arg Ala Pro Gln Asp Asn Lys Asn
    50                  55                  60

His Gln Val Ser Leu Ser Lys Gln Pro Thr Ser Arg Ala Arg Gly Asp
```

-continued

```
65                  70                  75                  80

Pro Thr Gly Gln Glu Glu Ser Lys Glu Lys Val Glu Lys Glu Thr Val
                85                  90                  95

Val Asp Pro Val Thr
            100


<210> SEQ ID NO 14
<211> LENGTH: 4
<212> TYPE: PRT
<213> ORGANISM: Artificial Sequence
<220> FEATURE:
<223> OTHER INFORMATION: ER retention seqeunce

<400> SEQUENCE: 14

Lys Asp Glu Leu
1


<210> SEQ ID NO 15
<211> LENGTH: 6
<212> TYPE: PRT
<213> ORGANISM: Artificial Sequence
<220> FEATURE:
<223> OTHER INFORMATION: Linker
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 15

Arg Xaa Arg Xaa Lys Arg
1               5


<210> SEQ ID NO 16
<211> LENGTH: 12
<212> TYPE: PRT
<213> ORGANISM: Artificial Sequence
<220> FEATURE:
<223> OTHER INFORMATION: ER retention sequence

<400> SEQUENCE: 16

Lys Lys Asp Leu Arg Asp Glu Leu Lys Asp Glu Leu
1               5                   10


<210> SEQ ID NO 17
<211> LENGTH: 13
<212> TYPE: PRT
<213> ORGANISM: Artificial Sequence
<220> FEATURE:
<223> OTHER INFORMATION: ER retention sequence

<400> SEQUENCE: 17

Lys Lys Asp Glu Leu Arg Asp Glu Leu Lys Asp Glu Leu
1               5                   10


<210> SEQ ID NO 18
<211> LENGTH: 13
<212> TYPE: PRT
<213> ORGANISM: Artificial Sequence
<220> FEATURE:
<223> OTHER INFORMATION: ER retention sequence

<400> SEQUENCE: 18

Lys Lys Asp Glu Leu Arg Val Glu Leu Lys Asp Glu Leu
```

```
1               5                   10


<210> SEQ ID NO 19
<211> LENGTH: 12
<212> TYPE: PRT
<213> ORGANISM: Artificial Sequence
<220> FEATURE:
<223> OTHER INFORMATION: ER retention sequence

<400> SEQUENCE: 19

Lys Asp Glu Leu Lys Asp Glu Leu Lys Asp Glu Leu
1               5                   10


<210> SEQ ID NO 20
<211> LENGTH: 46
<212> TYPE: PRT
<213> ORGANISM: Pseudomonas aeruginosa

<400> SEQUENCE: 20

Pro Leu Glu Thr Phe Thr Arg His Arg Gln Pro Arg Gly Trp Glu Gln
1               5                   10                  15

Leu Glu Gln Cys Gly Tyr Pro Val Gln Arg Leu Val Ala Leu Tyr Leu
            20                  25                  30

Ala Ala Arg Leu Ser Trp Asn Gln Val Asp Gln Val Ile Arg
        35                  40                  45


<210> SEQ ID NO 21
<211> LENGTH: 68
<212> TYPE: PRT
<213> ORGANISM: Artificial Sequence
<220> FEATURE:
<223> OTHER INFORMATION: mCD28convPEt

<400> SEQUENCE: 21

Thr Asp Ile Tyr Phe Cys Lys Ile Glu Phe Met Tyr Pro Pro Pro Tyr
1               5                   10                  15

Leu Asp Asn Glu Lys Ser Asn Gly Thr Ile Ile His Arg Ala Arg Tyr
            20                  25                  30

Lys Arg Gly Trp Glu Gln Leu Glu Gln Cys Gly Tyr Pro Val Gln Arg
        35                  40                  45

Leu Val Ala Leu Tyr Leu Ala Ala Arg Leu Ser Trp Asn Gln Val Asp
    50                  55                  60

Gln Val Ile Arg
65


<210> SEQ ID NO 22
<211> LENGTH: 68
<212> TYPE: PRT
<213> ORGANISM: Artificial Sequence
<220> FEATURE:
<223> OTHER INFORMATION: hCD28convPEt

<400> SEQUENCE: 22

Thr Asp Ile Tyr Phe Cys Lys Ile Glu Val Met Tyr Pro Pro Pro Tyr
1               5                   10                  15

Leu Asp Asn Glu Lys Ser Asn Gly Thr Ile Ile His Arg Ala Arg Tyr
            20                  25                  30

Lys Arg Gly Trp Glu Gln Leu Glu Gln Cys Gly Tyr Pro Val Gln Arg
        35                  40                  45

Leu Val Ala Leu Tyr Leu Ala Ala Arg Leu Ser Trp Asn Gln Val Asp
    50                  55                  60
```

```
Gln Val Ile Arg
65


<210> SEQ ID NO 23
<211> LENGTH: 124
<212> TYPE: PRT
<213> ORGANISM: Artificial Sequence
<220> FEATURE:
<223> OTHER INFORMATION: hepatitis B virus X protein deletion mutant

<400> SEQUENCE: 23

Met Ala Ala Arg Met Cys Cys Gln Leu Asp Pro Ala Arg Asp Val Leu
1               5                   10                  15

Cys Leu Arg Pro Ser His Leu Ser Leu Arg Gly Leu Pro Val Cys Ser
            20                  25                  30

Phe Ser Ser Ala Gly Pro Cys Ala Leu Arg Phe Thr Ser Ala Arg Arg
        35                  40                  45

Met Glu Thr Thr Val Asn Ala Pro Trp Ser Leu Pro Thr Val Leu His
    50                  55                  60

Lys Arg Thr Ile Gly Leu Ser Gly Arg Ser Met Thr Trp Ile Glu Glu
65                  70                  75                  80

Tyr Ile Lys Asp Cys Val Phe Lys Asp Trp Glu Glu Leu Gly Glu Glu
                85                  90                  95

Ile Arg Leu Lys Val Phe Val Leu Gly Gly Cys Arg His Lys Leu Val
            100                 105                 110

Cys Ser Pro Ala Pro Cys Asn Phe Phe Thr Ser Ala
        115                 120


<210> SEQ ID NO 24
<211> LENGTH: 154
<212> TYPE: PRT
<213> ORGANISM: Hepatitis B virus

<400> SEQUENCE: 24

Met Ala Ala Arg Met Cys Cys Gln Leu Asp Pro Ala Arg Asp Val Leu
1               5                   10                  15

Cys Leu Arg Pro Val Gly Ala Glu Ser Arg Gly Arg Pro Leu Pro Gly
            20                  25                  30

Pro Leu Gly Ala Leu Pro Pro Ser Ser Ala Ser Ala Val Pro Ala Asp
        35                  40                  45

His Gly Ser His Leu Ser Leu Arg Gly Leu Pro Val Cys Ser Phe Ser
    50                  55                  60

Ser Ala Gly Pro Cys Ala Leu Arg Phe Thr Ser Ala Arg Arg Met Glu
65                  70                  75                  80

Thr Thr Val Asn Ala Pro Trp Ser Leu Pro Thr Val Leu His Lys Arg
                85                  90                  95

Thr Ile Gly Leu Ser Gly Arg Ser Met Thr Trp Ile Glu Glu Tyr Ile
            100                 105                 110

Lys Asp Cys Val Phe Lys Asp Trp Glu Glu Leu Gly Glu Glu Ile Arg
        115                 120                 125

Leu Lys Val Phe Val Leu Gly Gly Cys Arg His Lys Leu Val Cys Ser
    130                 135                 140

Pro Ala Pro Cys Asn Phe Phe Thr Ser Ala
145                 150


<210> SEQ ID NO 25
<211> LENGTH: 317
<212> TYPE: PRT
```

-continued

<213> ORGANISM: Artificial Sequence
<220> FEATURE:
<223> OTHER INFORMATION: RAP1-mCD28convPEt-deletion mutant HBx-K3

<400> SEQUENCE: 25

```
Met Ala Glu Phe Glu Glu Pro Arg Val Ile Asp Leu Trp Asp Leu Ala
1               5                   10                  15

Gln Ser Ala Asn Leu Thr Asp Lys Glu Leu Glu Ala Phe Arg Glu Glu
            20                  25                  30

Leu Lys His Phe Glu Ala Lys Ile Glu Lys His Asn His Tyr Gln Lys
        35                  40                  45

Gln Leu Glu Ile Ala His Glu Lys Leu Arg His Ala Glu Ser Val Gly
    50                  55                  60

Asp Gly Glu Arg Val Ser Arg Ser Arg Glu Lys His Ala Leu Leu Glu
65                  70                  75                  80

Gly Arg Thr Lys Glu Leu Gly Tyr Thr Val Lys Lys His Leu Gln Asp
                85                  90                  95

Leu Ser Gly Arg Ile Ser Arg Ala Arg Glu Leu Thr Asp Ile Tyr Phe
            100                 105                 110

Cys Lys Ile Glu Phe Met Tyr Pro Pro Pro Tyr Leu Asp Asn Glu Lys
        115                 120                 125

Ser Asn Gly Thr Ile Ile His Arg Ala Arg Tyr Lys Arg Gly Trp Glu
    130                 135                 140

Gln Leu Glu Gln Cys Gly Tyr Pro Val Gln Arg Leu Val Ala Leu Tyr
145                 150                 155                 160

Leu Ala Ala Arg Leu Ser Trp Asn Gln Val Asp Gln Val Ile Arg Gly
                165                 170                 175

Ser Glu Phe Met Ala Ala Arg Met Cys Cys Gln Leu Asp Pro Ala Arg
            180                 185                 190

Asp Val Leu Cys Leu Arg Pro Ser His Leu Ser Leu Arg Gly Leu Pro
        195                 200                 205

Val Cys Ser Phe Ser Ser Ala Gly Pro Cys Ala Leu Arg Phe Thr Ser
    210                 215                 220

Ala Arg Arg Met Glu Thr Thr Val Asn Ala Pro Trp Ser Leu Pro Thr
225                 230                 235                 240

Val Leu His Lys Arg Thr Ile Gly Leu Ser Gly Arg Ser Met Thr Trp
                245                 250                 255

Ile Glu Glu Tyr Ile Lys Asp Cys Val Phe Lys Asp Trp Glu Glu Leu
            260                 265                 270

Gly Glu Glu Ile Arg Leu Lys Val Phe Val Leu Gly Gly Cys Arg His
        275                 280                 285

Lys Leu Val Cys Ser Pro Ala Pro Cys Asn Phe Phe Thr Ser Ala Leu
    290                 295                 300

Glu Lys Asp Glu Leu Lys Asp Glu Leu Lys Asp Glu Leu
305                 310                 315
```

<210> SEQ ID NO 26
<211> LENGTH: 317
<212> TYPE: PRT
<213> ORGANISM: Artificial Sequence
<220> FEATURE:
<223> OTHER INFORMATION: RAP1-hCD28convPEt-deletion mutant HBx-K3

<400> SEQUENCE: 26

```
Met Ala Glu Phe Glu Glu Pro Arg Val Ile Asp Leu Trp Asp Leu Ala
1               5                   10                  15
```

-continued

```
Gln Ser Ala Asn Leu Thr Asp Lys Glu Leu Glu Ala Phe Arg Glu Glu
            20                  25                  30

Leu Lys His Phe Glu Ala Lys Ile Glu Lys His Asn His Tyr Gln Lys
        35                  40                  45

Gln Leu Glu Ile Ala His Glu Lys Leu Arg His Ala Glu Ser Val Gly
    50                  55                  60

Asp Gly Glu Arg Val Ser Arg Ser Arg Glu Lys His Ala Leu Leu Glu
65                  70                  75                  80

Gly Arg Thr Lys Glu Leu Gly Tyr Thr Val Lys Lys His Leu Gln Asp
                85                  90                  95

Leu Ser Gly Arg Ile Ser Arg Ala Arg Glu Leu Thr Asp Ile Tyr Phe
            100                 105                 110

Cys Lys Ile Glu Val Met Tyr Pro Pro Pro Tyr Leu Asp Asn Glu Lys
        115                 120                 125

Ser Asn Gly Thr Ile Ile His Arg Ala Arg Tyr Lys Arg Gly Trp Glu
    130                 135                 140

Gln Leu Glu Gln Cys Gly Tyr Pro Val Gln Arg Leu Val Ala Leu Tyr
145                 150                 155                 160

Leu Ala Ala Arg Leu Ser Trp Asn Gln Val Asp Gln Val Ile Arg Gly
                165                 170                 175

Ser Glu Phe Met Ala Ala Arg Met Cys Cys Gln Leu Asp Pro Ala Arg
            180                 185                 190

Asp Val Leu Cys Leu Arg Pro Ser His Leu Ser Leu Arg Gly Leu Pro
        195                 200                 205

Val Cys Ser Phe Ser Ser Ala Gly Pro Cys Ala Leu Arg Phe Thr Ser
    210                 215                 220

Ala Arg Arg Met Glu Thr Thr Val Asn Ala Pro Trp Ser Leu Pro Thr
225                 230                 235                 240

Val Leu His Lys Arg Thr Ile Gly Leu Ser Gly Arg Ser Met Thr Trp
                245                 250                 255

Ile Glu Glu Tyr Ile Lys Asp Cys Val Phe Lys Asp Trp Glu Glu Leu
            260                 265                 270

Gly Glu Glu Ile Arg Leu Lys Val Phe Val Leu Gly Gly Cys Arg His
        275                 280                 285

Lys Leu Val Cys Ser Pro Ala Pro Cys Asn Phe Phe Thr Ser Ala Leu
    290                 295                 300

Glu Lys Asp Glu Leu Lys Asp Glu Leu Lys Asp Glu Leu
305                 310                 315
```

<210> SEQ ID NO 27
<211> LENGTH: 68
<212> TYPE: PRT
<213> ORGANISM: Artificial Sequence
<220> FEATURE:
<223> OTHER INFORMATION: CD28convPEt
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (30)..(30)

-continued

<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid

<400> SEQUENCE: 27

Thr Asp Ile Tyr Phe Cys Lys Xaa Glu Xaa Xaa Tyr Pro Pro Pro Tyr
1               5                   10                  15

Xaa Asp Asn Glu Lys Ser Asn Gly Thr Ile Ile His Arg Xaa Arg Xaa
            20                  25                  30

Lys Arg Gly Trp Glu Gln Leu Glu Gln Cys Gly Tyr Pro Val Gln Arg
        35                  40                  45

Leu Val Ala Leu Tyr Leu Ala Ala Arg Leu Ser Trp Asn Gln Val Asp
    50                  55                  60

Gln Val Ile Arg
65

<210> SEQ ID NO 28
<211> LENGTH: 28
<212> TYPE: PRT
<213> ORGANISM: Artificial Sequence
<220> FEATURE:
<223> OTHER INFORMATION: CD28 consensus sequence
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid

<400> SEQUENCE: 28

Thr Asp Ile Tyr Phe Cys Lys Xaa Glu Xaa Xaa Tyr Pro Pro Pro Tyr
1               5                   10                  15

Xaa Asp Asn Glu Lys Ser Asn Gly Thr Ile Ile His
            20                  25

<210> SEQ ID NO 29
<211> LENGTH: 10
<212> TYPE: PRT
<213> ORGANISM: Artificial Sequence
<220> FEATURE:
<223> OTHER INFORMATION: CD28 critical region
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid

<400> SEQUENCE: 29

Lys Xaa Glu Xaa Xaa Tyr Pro Pro Pro Tyr
1               5                   10

<210> SEQ ID NO 30
<211> LENGTH: 61
<212> TYPE: PRT
<213> ORGANISM: Pseudomonas aeruginosa

<400> SEQUENCE: 30

-continued

```
Gly Gly Ser Leu Ala Ala Leu Thr Ala His Gln Ala Cys His Leu Pro
1               5                   10                  15

Leu Glu Thr Phe Thr Arg His Arg Gln Pro Arg Gly Trp Glu Gln Leu
            20                  25                  30

Glu Gln Cys Gly Tyr Pro Val Gln Arg Leu Val Ala Leu Tyr Leu Ala
        35                  40                  45

Ala Arg Leu Ser Trp Asn Gln Val Asp Gln Val Ile Arg
    50                  55                  60


<210> SEQ ID NO 31
<211> LENGTH: 27
<212> TYPE: DNA
<213> ORGANISM: Artificial Sequence
<220> FEATURE:
<223> OTHER INFORMATION: HBV1-F'-EcoRI

<400> SEQUENCE: 31

gaattcatgg ctgctcgtat gtgctgc                                          27


<210> SEQ ID NO 32
<211> LENGTH: 29
<212> TYPE: DNA
<213> ORGANISM: Artificial Sequence
<220> FEATURE:
<223> OTHER INFORMATION: HBV20.51-S

<400> SEQUENCE: 32

ctgcgtccgt ctcacctgtc tctgcgtgg                                        29


<210> SEQ ID NO 33
<211> LENGTH: 58
<212> TYPE: DNA
<213> ORGANISM: Artificial Sequence
<220> FEATURE:
<223> OTHER INFORMATION: HBV20.51-A

<400> SEQUENCE: 33

gttctgtgcc tgcgtccgtc tcacctgtcg acaggtgaga cggacgcagg cacagaac       58


<210> SEQ ID NO 34
<211> LENGTH: 28
<212> TYPE: DNA
<213> ORGANISM: Artificial Sequence
<220> FEATURE:
<223> OTHER INFORMATION: HBV154-R'-XhoI

<400> SEQUENCE: 34

ctcgagggca gaggtgaaga agttgcac                                         28
```

HEPATITIS B THERAPEUTIC VACCINES

REFERENCE TO RELATED APPLICATION

The present application claims the priority to U.S. Provisional Application Ser. No. 62/396,642, filed Sep. 19, 2016, which is herein incorporated by reference in its entirety.

FIELD OF THE INVENTION

The present invention relates generally to hepatitis B, and more specifically to hepatitis B vaccines.

BACKGROUND OF THE INVENTION

According to 2017 WHO global hepatitis report, worldwide there are 257 million people carrying hepatitis B virus (HBV). HBV infection has been known to cause a series of liver disease, including liver inflammation, liver cirrhosis, and hepatocelllular carcinoma (HCC), etc., in which HBV X protein (HBx) plays an important role.

HBx when expressed in bacteria is insoluble. Dong Liu et al. developed a method for obtaining soluble HBx by using maltose binding protein tag (MBP-tag), eliminating the need for denaturation and renaturation (*Biotechnol. Appl. Biochem.* 2009, 54:141-147). The disadvantage of their method is its complexity. It requires amylose resin and Q-Sepharose chromatography for purification, and Factor Xa enzyme digestion for 48 hrs to remove the MBP-tag. These steps add to the complexity of the purification process, increasing cost and time and limiting its use in large-scale productions. Others have prepared HBx protein by denaturing and renaturing inclusion bodies, then metal affinity chromatography (with $Ni^{2+}$ sepharose column). This method has problems of Nickel toxicity (Forgacs Z et al. (2012), *J Environ Sci Health A Tox Hazard Subst Environ Eng,* 47(9): 1249-60), thus limiting its use in drug manufacturing processes.

U.S. Pat. No. 9,481,714 B2 discloses a fusion protein RAP1-CD28convPEt-$HBx_{1-154}$-K3, which had a similar problem with aggregate formation. A high concentration of urea was needed during the process of making the RAP1-CD28convPEt-$HBx_{1-154}$-K3 for destroying hydrogen bonds within the protein to denature and solubilize the recombinant protein inside the inclusion bodies. However, a final removal of urea to refold the RAP1-$CD28_{conv}$PEt-$HBxt_{1-154}$-K3 could easily cause formation of aggregates and thus precipitation, leading to a poor yield.

There is therefore a need to develop a novel therapeutic HBV vaccine and new method of preparing it.

SUMMARY OF THE INVENTION

It was discovered that without affecting the protein structure and function, a deletion of a fragment ranging from the amino acid residue 21 to the amino acid residue 50 of HBx by DNA engineering technique could solve the problems of easy aggregation and precipitation during protein refolding, and increase final protein production yield.

In one aspect, the invention relates to a fusion protein comprising:

(a) an antigen-presenting cell (APC)-binding domain or a CD91 receptor-binding domain, located at the N-terminus of the fusion protein;

(b) a protein transduction domain, located at the C-terminus of the APC-binding domain or the CD91 receptor-binding domain, wherein the protein transduction domain is a fusion polypeptide comprising:

(1) a T cell sensitizing signal-transducing peptide consisting of 28-53 amino acid residues in length, comprising the amino acid sequence of SEQ ID NO: 28, in which $Xaa^8$ is I or L; $Xaa^{10}$ is V. F or A, $Xaa^{11}$ is M or L, $Xaa^{17}$ is L or I, being located at the N-terminus of the fusion polypeptide;

(2) a translocation peptide consisting of 34-112 amino acid residues in length, comprising an amino acid sequence that is at least 90% identical to SEQ ID NO: 3, 4, 20 or 30; and (3) a linker linking the T cell sensitizing signal-transducing peptide and the translocation peptide; and (c) an antigen comprising a hepatitis B virus X protein deletion mutant (ΔHBx) that lacks residues at least from amino acid residue 21 to amino acid residue 50, located at the C-terminus of the protein transduction domain.

In another aspect, the invention relates to a vaccine composition comprising: (a) a therapeutically effective amount of the fusion protein according to the invention; and (b) an adjuvant. The adjuvant may comprise CpG oligodeoxynucleotide.

Further in another aspect, the invention relates to use of a fusion protein according to the invention in the manufacture of a medicament for inducing a hepatitis B virus X protein (HBx)-specific T cell response, treating infection caused by hepatitis B virus, minimizing symptoms caused by hepatitis B virus infection, inhibiting proliferation of hepatitis B virus in liver cells, and/or suppressing hepatitis B virus infection in a subject in need thereof.

Further in another aspect, the invention relates to a fusion protein according to the invention for use in inducing a hepatitis B virus X protein (HBx)-specific T cell response, treating infection caused by hepatitis B virus, minimizing symptoms caused by hepatitis B virus infection, inhibiting proliferation of hepatitis B virus in liver cells, and/or suppressing hepatitis B virus infection in a subject in need thereof.

Alternatively, the invention also relates to a method for inducing a hepatitis B virus X protein (HBx)-specific T cell response, treating infection caused by hepatitis B virus, minimizing symptoms caused by hepatitis B virus infection, inhibiting proliferation of hepatitis B virus in liver cells, and/or suppressing hepatitis B virus infection in a subject in need thereof. The method comprises administering a therapeutically effective amount of the fusion protein of the invention to the subject in need thereof.

Yet in another aspect, the invention relates to a method for preparation of a hepatitis B virus X protein deletion mutant fusion protein, comprising: (a) generating a plasmid for expressing the fusion protein of the invention; (b) causing the plasmid to express the fusion protein within a host cell; and (c) collecting the fusion protein from the host cell.

In one embodiment of the invention, the APC-binding domain or the CD91 receptor-binding domain comprises an amino acid sequence that is at least 90% identical to the sequence selected from the group consisting of SEQ ID NOs: 5, 9, 6, 7, and 8.

In another embodiment, the fusion protein may further comprises an endoplasmic reticulum retention sequence located at the C-terminus of the fusion protein. In another embodiment, the fusion protein is free of an endoplasmic reticulum retention sequence at C-terminus thereof if the antigen contains 10 or more epitopes. In another embodiment, the protein transduction domain comprises the amino acid sequence of SEQ ID NO: 27. The protein transduction domain may comprise the amino acid sequence of SEQ ID NO: 22. In another embodiment, the APC-binding domain or the CD91 receptor-binding domain comprises an amino acid sequence selected from the group consisting of SEQ ID NOs: 5, 9, 6, 7, and 8. In another embodiment, the T cell sensitizing signal-transducing peptide comprises an amino acid sequence selected from the group consisting of SEQ ID NO: 1 and 2. In another embodiment, the translocation peptide comprises the amino acid sequence of SEQ ID NO: 3. In another embodiment, the antigen comprises the amino acid sequence of SEQ ID NO: 23. In another embodiment, the deletion mutant ΔHBx has a deletion of amino acids (aa) 1 to 50, or as S to 50, or as 10 to 50, or aa 15 to 50, or aa 18 to 50. In another embodiment, the deletion mutant ΔHBx has a deletion of amino acids from aa 1, as 2, as 3, aa 4, as 5, as 6, as 7, aa 8, aa 9, as 10, as 11, aa 12, as 13, aa 14, aa 15, aa 16, as 17, as 18, aa 19, aa 20, or aa 21 to as 50. In another embodiment, the antigen comprises a hepatitis B virus X protein deletion mutant (ΔHBx) with a deletion from the $21^{st}$ amino acid to $50^{th}$ amino acid.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention. Wherever possible, the same reference numbers are used throughout the drawings to refer to the same or like elements of an embodiment.

DETAILED DESCRIPTION OF THE INVENTION

Definitions

Figure 1:
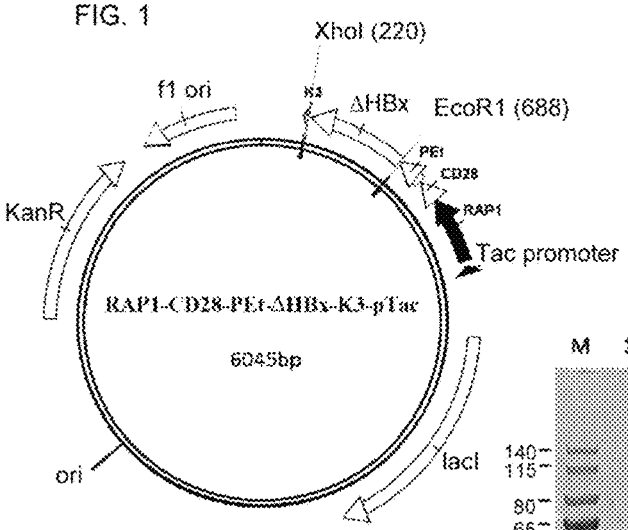
FIG. 1 is a vector map showing the plasmid RAP1-CD28conv-PEt-ΔHBx-K3-pTac.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

Immunogenic proteins such as fusion proteins for use as immunogenic enhancers for inducing antigen-specific T cell responses are disclosed in the U.S. Pat. Nos. 9,481,714 B2, 9,339,536 B2 and 20160250324 A1, each of which is incorporated herein by reference in its entirety.

The term "an antigen-presenting cell (APC)-binding domain" refers to a domain (which is a polypeptide) that can bind to an antigen-presenting cell (APC). In an embodiment, the APC-binding domain is selected from the group consisting of receptor-associated protein-1 (RAP1) domain III, alpha-2-macroglobulin receptor-associated protein (A2M), HIV-Tat, and heat shock proteins (HSPs), and *Pseudomonas* exotoxin A (PE) binding domain I. In another embodiment, the APC-binding domain may be a polypeptide comprising an amino acid sequence that is at least 90% identical to the sequence selected from the group consisting of SEQ ID NOs: 5, 6, 7, 8, and 9.

Cluster of differentiation 91 (CD91) is a protein that forms a receptor found in the plasma membrane of cells and is involved in receptor-mediated endocytosis.

In another embodiment of the invention, the APC-binding domain or the CD91 receptor-binding domain exhibits a characteristics of recognizing and binding to a receptor on an antigen-presenting cell (APC) selected from the group consisting of dendritic cells, monocytes, B-cells and lymphocytes.

Receptor-associated protein (RAP1) with a molecular weight of 39 kDa is an ER resident protein and molecular chaperone for LDL receptor-related protein. It has a high binding affinity to CD91 (Kd~3 nM) and is composed by three functional-similar domain.

The term "a protein transduction domain" is a polypeptide whose function is to sensitize T-cells and thus enhance antigen-specific T cell response, and/or to guide or direct an antigen toward (i.e., to target to) class I major histocompatibility complex (MHC-I) pathway (i.e., a cytotoxic T cell pathway) of antigen presentation.

The term "to sensitize T cells" generally means that CD8+ and CD4+ T cells are sensitized and as a result, CD8+ (CTL) and CD4+ T cell responses to an antigen challenge are enhanced. An antigen-specific cytotoxic cell (CTL) response is measured by quantifying the production of antigen-specific induced γ-interferon in response to an antigen. For example, without a sensitization signal, an antigen alone may induce weak or no CTL response at all, i.e., weak or no production of antigen-specific γ-interferon, while in the presence of a sensitization signal, the antigen may induce an enhanced CTL response. Thus, the function of a sensitization signal is to sensitize CD8+ T cells in a host so that when the host is later challenged by an antigen, the antigen can induce an enhanced antigen-specific CTL response due to prior CD8+ T cell sensitization.

In addition, CD4+ T cell response is also enhanced by prior T cell sensitization. An antigen-specific CD4+ T cell response is indirectly measured by antibtxody (IgG) titer production from B cells.

A protein transduction domain may be a peptide and/or fusion polypeptide selected from the group consisting of:

(i) a T cell-sensitizing signal-transducing peptide of 28-53 amino acid residues in length, comprising the amino acid sequence that is at least 90% identical to SEQ ID NO: 1;

(ii) a translocation peptide of 34-12 amino acid residues in length, comprising the amino acid sequence that is at least 90% identical to SEQ ID NO: 3; and (iii) a fusion polypeptide, comprising the T cell sensitizing signal-transducing peptide and the translocation peptide, wherein the T cell sensitizing signal-transducing peptide is located at the N-terminus of the fusion polypeptide In another embodiment of the invention, the protein transduction domain may be "a fusion polypeptide", in which the fusion polypeptide comprises a T cell sensitizing signal-transducing peptide, a linker, and a translocation peptide. For example, the fusion polypeptide may be the polypeptide "$CD28_{conv}PE_t$", which comprises a linker between the "$CD28_{conv}$" and the "$PE_t$".

The term "$CD28_{conv}$" refers to a CD28 conserved region, which is a "T cell sensitizing signal-transducing peptide". It's an epitope for inducing CD28 agonist antibody.

The term "$PE_t$" or "$PE_t$Core" refers to a PE translocation domain core with 34 amino acid residues in length.

The orientation or arrangement of the fusion polypeptide "$CD28_{conv}PE_t$" is important in that "$CD28_{conv}$" (or the T cell sensitizing signal-transducing peptide) must be at the upstream to the $PE_t$ (or the translocation peptide), i.e., $PE_t$ must be at the C-terminus of the "$CD28_{conv}$" to obtain enhanced T-cell responses. The "$CD28_{conv}PE_t$" can raise much higher IgG titer (called CD28-specific agonist antibody) specific to $CD28_{conv}$ than the reversed orientation fusion peptide $PE_tCD28_{conv}$. The CD28-specific agonist antibody can sensitize both CD4+ and CD8+ T cells. The correct orientation fusion polypeptide $CD28_{conv}PE_t$ contains a linker ($R^1X^2R^3X^4K^5R^6$) between $CD28_{conv}$ and $PE_t$ domains. The linker contains an antigen presenting cell (APC)-specific protease (cathepsin L) cutting site Lys-Arg (KR). Therefore, the fusion protein RAP1-$CD28_{conv}PE_t$-Antigen-K3 can be digested into the two fragments: RAP1-$CD28_{conv}$ and $PE_t$-Antigen-K3. The RAP1-$CD28_{conv}$ fragment can be further digested in the lysosome and the epitope of $CD28_{conv}$ is then presented to the APC cell surface via MHC II pathway, which in turn elicits a humoral immune response producing CD28 agonist antibody. Thus, CD28 agonist antibody is produced by B cells. This CD28 agonist antibody can bind to CD28 on the T cell surface and pre-activate the T cells (CD4+ and CD8+ T cells).

A "T cell-sensitizing signal-transducing peptide" has 28-53 amino acid residues in length and comprises an amino acid sequence that is at least 90% identical to SEQ ID NO: 28, in which $X^8$ is I or L; $X^{10}$ is V, F or A, $X^{11}$ is M or L, $X^{17}$ is L or I.

The T cell-sensitizing signal-transducing peptide comprises the critical region $K^1X^2E^3X^4X^5Y^6P^7P^8P^9Y^{10}$ (SEQ ID NO: 29), wherein $X^2$ is I or L; $X^4$ is V, F or A, $X^5$ is M or L.

A T cell sensitizing signal-transducing peptide (TDIYFCKIEFMYPPPYLDNEKSNGTIIH; SEQ ID NO: 28, wherein $X^8$ is 1, $X^{10}$ is F, $X^{11}$ is M, $X^{17}$ is L) specific for mice was illustrated in the U.S. Pat. No. 9,481,714 B2.

A PE translocation peptide may comprise an amino acid sequence that is at least 90% identical to SEQ ID NO: 3, 4, 20 or 30. For example, the amino acid sequence of a PE translocation peptide may be a.a. 280-a.a. 313 (SEQ ID NO: 3), a.a. 268-a.a. 313 (SEQ ID NO: 20), a.a. 253-a.a. 313 (SEQ ID NO: 30), or a.a. 253-a.a. 364 (SEQ ID NO: 4) of full length PE (SEQ ID NO: 10). That is, the amino acid sequence of a PE translocation peptide may contain any region of the PE domain II (a.a. 253 to a.a. 364; SEQ ID NO: 4) as long as it comprises a.a. 280-a.a. 313 (SEQ ID NO: 3) essential fragment.

The function of an endoplasmic reticulum (ER) retention sequence is to assist translocation of an antigen from an endocytic compartment into ER and retains it in the lumen. It comprises the sequence Lys Asp Glu Leu (KDEL) or RDEL. For example, an ER retention sequence may comprise the sequence of KKDLRDELKDEL (SEQ ID NO: 16), KKDELRDELKDEL (SEQ ID NO: 17), KKDELRVELKDEL (SEQ ID NO: 18) or KDELKDELKDEL (SEQ ID NO: 19).

Two fusion protein with deletion HBx mutants were generated, one with a deletion of $1^{st}$-$50^{th}$ amino acids, the other with a deletion of $21^{st}$-$50^{th}$ amino acids. The fusion protein RAP1-$CD28_{conv}$PEt-ΔHBx-K3 according to the invention was equally effective as the fusion protein RAP1-$CD28_{conv}$PEt-HBx-K3 (with the full-length HBx), but the former exhibited a much better stability than the latter. After being storaged for a certain time period such as one year, the fusion protein RAP1-$CD28_{conv}$PEt-HBx-K3 in a liquid form showed 100% aggregation, while the fusion protein RAP1-$CD28_{conv}$PEt-ΔHBx-K3 exhibited less aggregation.

Oligodeoxyribonucleotides containing CpG motifs (CpG ODNs) are widely used for activation of immune cells.

The term "subject" refers to a human or a non-human animal.

The term "treating" or "treatment" refers to administration of an effective amount of the fusion protein to a subject in need thereof, who has cancer or infection, or a symptom or predisposition toward such a disease, with the purpose of cure, alleviate, relieve, remedy, ameliorate, or prevent the disease, the symptoms of it, or the predisposition towards it. Such a subject can be identified by a health care professional based on results from any suitable diagnostic method.

The term "an effective amount" refers to the amount of an active compound that is required to confer a therapeutic effect on the treated subject. Effective doses will vary, as recognized by those skilled in the art, depending on rout of administration, excipient usage, and the possibility of co-usage with other therapeutic treatment.

Abbreviations

CD 28, Cluster of Differentiation 28.

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Methods

Preparation of the Fusion Protein RAP1-$CD28_{conv}$PEt-ΔHBx-K3

1. Construction of the plasmid RAP1-CD28-PEt-ΔHBx-K3-pTac

The following primers were used:

```
HBV1-F'-EcoRI:
                                     (SEQ ID NO: 31)
GAATTCATGGCTGCTCGTATGTGCTGC;

HBV20.51-S:
                                     (SEQ ID NO: 32)
CTGCGTCCGTCTCACCTGTCTCTGCGTGG;

HBV20.51-A:
                                     (SEQ ID NO: 33)
GTTCTGTGCCTGCGTCCGTCTCACCTGTCGACAGGTGAGACGGACGCAGG

CACAGAAC;

HBV154-R'-XhoI:
                                     (SEQ ID NO: 34)
CTCGAGGGCAGAGGTGAAGAAGTTGCAC.
```

Using the fusion protein RAP1-$CD28_{conv}$PEt-$HBx_{1-154}$-K3-pTac disclosed in the U.S. Pat. No. 9,481,714 B2 as a DNA template (See FIGS. 10 and 11, No. 8), the primers SEQ ID NOs. 31-34 were used to synthesize $HBx_{1-20}$ and $HBx_{51-154}$ fragments by polymerase chain reaction, respectively. The primers HBV20.51-S and HBV20.51-A were designed to have a portion of sequences forming overlapping complementary sequences, and thus $HBx_{1-20}$ and $HBx_{51-154}$ fragments could overlap and complement each other to form a template in a polymerase chain reaction and the primers HBV1-F'-EcoRI and HBV154-R'-XhoI were used to multiply in the chain reaction, and finally produced $ΔHBx_{(1-20,\ 51-154)}$ fragment containing EcoRI, XhoI restriction endonuclease cleavage sites. The EcoRI and XhoI cutting sites on the $ΔHBx_{(1-20,\ 51-154)}$ fragment allowed insertion of the $ΔHBx_{(1-20,\ 51-154)}$ fragment into the RAP1-K3-pTac plasmid (see U.S. Pat. No. 9,481,714 B2, FIG. 10) to obtain the construct RAP1-ΔHBx-K3-pTac. The fragments $mCD28_{conv}$ and $hCD28_{conv}$ containing MfeI and EcoRI cutting sites were obtained by using gene synthesis.

Utilizing MfeI and EcoRI cutting sites, the fragments $mCD28_{conv}$ and $hCD28_{conv}$ were separately inserted into the EcoR site of the RAP1-ΔHBx-K3-pTac plasmid to generate the constructs RAP1-$mCD28_{conv}$ PEt-ΔHBx-K3-pTac and RAP1-$hCD28_{conv}$ PEt-ΔHBx-K3-pTac, respectively.

2. RAP1-$CD28_{conv}$ PEt-ΔHBx-K3 Comprises RAP1, CD28conv, PEt, ΔHBx, Etc. Components.

Table 1 shows sequences of various components that may be used to prepare a fusion protein according to the invention.

TABLE 1

| Component | SEQ ID NO: | Length (resdues) |
|---|---|---|
| hCD28 Core | 1 | 28 |
| hCD28 Maximum | 2 | 53 |
| $PE_t$ Core (PE translocation domain core; a.a. 280- a.a. 313 of PE) | 3 | 34 |
| $PE_t$ Maximum (translocation domain maxi, a.a. 253 - a.a. 364 of PE) | 4 | 112 |
| RAP1 Minimum (domain III of RAP1) | 5 | 104 |
| A2M Minimum | 6 | 151 |
| HIV-Tat Minimum | 7 | 24 |
| HSPs Minimum, Heat shock 70 kDa protein (HSPs; *Homo sapiens*) | 8 | 641 |

TABLE 1-continued

| Component | SEQ ID NO: | Length (resdues) |
|---|---|---|
| Minimum *Pseudomonas* exotoxin A (PE) binding domain 1a (an APC-binding domain, a.a. 1- a.a. 252 of PE) | 9 | 252 |
| Full length PE (Exotoxin A mature form *Pseudomonas aeruginosa*) | 10 | 613 |
| Full length RAP1 (*Homo sapiens* low density lipoprotein receptor-related protein associated pro-tein 1, LRPAP1); Domain 1: a.a. 1- a.a. 112; domain 2: a.a. 113 - a.a. 218; domain 3: a.a. 219 - a.a. 323. | 11 | 323 |
| Full length A2M (*Homo sapiens* alpha-2-macroglobulin receptor-associated protein precursor) | 12 | 357 |
| HIV-Tat (Human immunodeficiency virus 1) | 13 | 101 |
| KDEL | 14 | 4 |
| Linker RXRXKR, in which "X" is any amino acid residue. | 15 | 6 |
| KKDLRDELKDEL | 16 | 12 |
| KKDELRDELKDEL | 17 | 13 |
| KKDEERVELKDEL | 18 | 13 |
| KDELKDELKDEL (K3) | 19 | 12 |
| $PE_{268-313}$ | 20 | 46 |
| $CD28_{conv}$PEt(w/mCD28) | 21 | 68 |
| $CD28_{conv}$PEt (w/hCD28) | 22 | 68 |
| hepatitis B virus X protein deletion mutant (ΔHBx) 124 a.a. (a.a. 1-20 a.a. + a.a. 51-154)* | 23 | 124 |
| Full-length hepatitis B virus X protein (HBx) | 24 | 154 |
| RAP1-$CD28_{conv}$PEt-ΔHBx-K3 (w/mCD28) | 25 | 317 |
| RAP1-$CD28_{conv}$PEt-ΔHBx-K3 (w/hCD28) | 26 | 317 |
| $CD28_{conv}PE_{t}$ $T^{1}D^{2}I^{3}Y^{4}F^{5}C^{6}K^{7}(X)^{8}E^{9}(X)^{10}(X)^{11}Y^{12}P^{13}P^{14}P^{15}Y^{16}(X)^{17}D^{18}N^{19}E^{20}K^{21}$ $S^{22}N^{23}G^{24}T^{25}I^{26}I^{27}H^{28}R^{29}(X)^{30}R^{31}(X)^{32}K^{33}R^{34}G^{35}W^{36}E^{37}Q^{38}L^{39}E^{40}Q^{41}$ $C^{42}G^{43}Y^{44}P^{45}V^{46}Q^{47}R^{48}L^{49}V^{50}A^{51}L^{52}Y^{53}L^{54}A^{55}A^{56}R^{57}L^{58}S^{59}W^{60}N^{61}Q^{62}$ $V^{63}D^{64}Q^{65}V^{66}I^{67}R^{68}$, wherein $(X)^{8}$ is I or L; $(X)^{10}$ is V, F or A, $(X)^{11}$ is M or L, $(X)^{17}$ is L or I, $(X)^{30,32}$ is any amino acid residue. | 27 | 68 |
| CD28 consensus sequence ($CD28_{conv}$) $T^{1}D^{2}I^{3}Y^{4}F^{5}C^{6}K^{7}(X)^{8}E^{9}(X)^{10}(X)^{11}Y^{12}P^{13}P^{14}P^{15}Y^{16}(X)^{17}D^{18}N^{18}E^{20}K^{21}$ $S^{22}N^{23}G^{24}T^{25}I^{26}I^{27}H^{28}$, wherein $(X)^{8}$ is I or L; $(X)^{10}$ is V, F or A, $(X)^{11}$ is M or L, $(X)^{17}$ is L or I. | 28 | 28 |
| CD28 critical region | 29 | 10 |
| $PE_{253-313}$ | 30 | 61 |

*: ΔHBx is a mutant with a deletion of residues from a.a. $21^{st}$ to a.a. $50^{th}$.

3. Production of Fusion Proteins:

Briefly, *Escherichia coli* BL21 cells containing the plasmid of interest from Master Cell Bank were thawed, and diluted 100 folds with a culture medium, and cultured at 30° C. with agitation at 250 rpm for 15 hrs. Afterwards, the BL21 cells were placed in a fermentation tank containing the culture medium, diluted to $OD_{600}$=0.5, continued to culture under the condition of 37° C., pH 7.0, 40% dissolved oxygen for 4 hrs, and fed with 70% glucose solution. When the $OD_{600}$ reached 20, 0.2 M isopropyl-β-D-thiogalactopyranoside (IPTG) was added to induce protein expression for 4 hrs. The induced *E. coli* was subjected to centrifugation at 4° C., 7000 rpm for 15 minutes, and a cell pellet was collected and stored at −80° C.

To recover the fusion protein, the cell pellet was re-suspended, sonicated to break the cells, and centrifuged at 9500 rpm, 4° C. for 15 minutes to separate and precipitate the inclusion bodies. The inclusion bodies were washed several times, added with a buffer solution containing 8M urea and 10 mM DTT, and then placed at 4° C. for overnight to solubilize the recombinant protein within the inclusion bodies. The buffer solution containing the solubilized protein was centrifuged at 9500 rpm, 4° C. for 2 minutes, the supernatant was filtered through a 0.2 μm filter and the filtrate collected. The filtrate was purified by ion-exchange chromatography, in which a DEAE sepharose was used as a solid phase and the elution buffer contained 8M urea, 1 mM DTT, 30-200 mM NaCl (pH 8.8).

The eluate purified from the ion exchange chromatography was collected, followed by dialysis (using 8-fold volume of buffer solution without urea, pH 5.0) to remove urea to allow renaturation (refolding) of the recombinant protein. The liquid was centrifuged at 9500 rpm, 4° C. for 15 minutes to form a supernatant and a precipitate (pellet), the supernatant was collected to thereby obtain a soluble fusion protein of interest.

ΔHBx Fusion Protein Comparative Efficacy Data and Verification:

The existing technology in the process of preparation of recombinant protein in the inclusion body has employed urea to disrupt protein hydrogen bonds, and the denatured recombinant protein is then renatured. During renaturation, inappropriate sequence may facilitate the misfolding of fusion protein RAP1-mCD28$_{conv}$PEt-HBx$_{1-154}$-K3 and lead to irreversible aggregate and precipitate. Using recombinant DNA techniques to remove the $21^{st}$-$50^{th}$ amino acid region of HBx, it was discovered that the fusion protein RAP1-mCD28$_{conv}$PEt-ΔHBx-K3 solved the problem of easy aggregation and sedimentation during protein refolding and thus, improved the final protein recovery yield.

The protein renaturation condition was tested on the dialyzed and purified fusion proteins RAP1-mCD28$_{conv}$PEt-HBx$_{1-154}$-K3 and RAP1-mCD2$_{conv}$PEt-ΔHBx-K3. It was found that after protein renaturation, more amount of RAP1-mCD28$_{conv}$PEt-ΔHBx-K3 (with deletion of HBX amino acid residues from a.a. 21 to a.a. $50^{th}$) retained soluble in the supernatant (FIG. 2, lanes 5 and 6) than RAP1-mCD28$_{conv}$PEt-HBx$_{1-154}$-K3 (without deletion of HBx a.a. $21^{st}$ to a.a. $50^{th}$) (FIG. 2, lanes 1 and 2).

Figure 2:
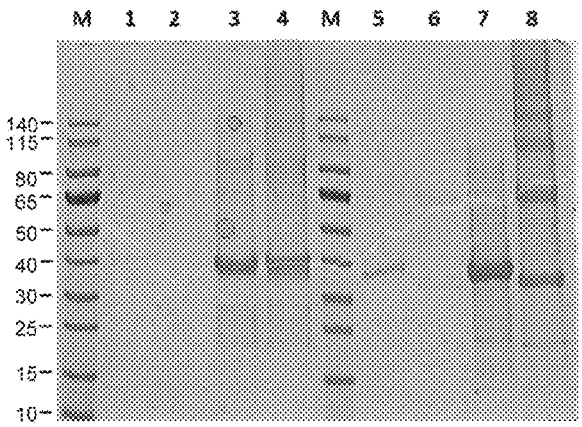
FIG. 2 is a photograph showing the results of gel electrophoresis.

Image analysis software was used to quantify the protein bands at 40 kDa (FIG. 2, lanes 1 to 8). The proportion of RAP1-mCD28$_{conv}$PEt-HBx$_{1-154}$-K3 remaining in the supernatant after refolding [computing lane 1/(lane 1+lane3)] was calculated as about 2.31%. After refolding, the RAP1-mCD28$_{conv}$PEt-ΔHBx-K3 retained in the supernatant was calculated as about 12.93% [computing the ratio of lane 5/(lane 5+lane 7)]. This indicates that removal of HBx $21^{st}$-$50^{th}$ amino acids can reduce aggregation and precipitation of the target protein during the refolding process, and improve the post-refolding recovery rate for more than 10%.

FIG. 2 shows a protein refolding comparison between RAP1-mCD28$_{conv}$PEt-HBx$_{1-154}$-K3 and RAP1-mCD28$_{conv}$PEt-ΔHBx-K3. Protein refolding was performed under the same protein concentration and dialysis conditions. After protein refolding, the supernatant and precipitate were respectively treated with or without a reducing agent (DTT), and analyzed by sodium dodecyl sulfate polyacrylamide gel electrophoresis (SDS-PAGE). M: protein marker ladder; Lane 1: after refolding, RAP1-mCD28$_{conv}$PEt-HBx$_{1-154}$-K3 refolding in the supernatant was treated with a reducing agent. Lane 2: After RAP1-mCD28$_{conv}$PEt-HBx$_{1-154}$-K3 refolding, the supernatant was not treated with a reducing agent; Lane 3: After RAP1-mCD28$_{conv}$PEt-HBx$_{1-154}$-K3 refolding, the precipitate was treated with a reducing agent. Lane 4: After RAP1-mCD28$_{conv}$PEt-HBx$_{1-154}$-K3 refolding, the precipitate was not treated with a reducing agent. Lane 5: After RAP1-mCD28$_{conv}$PEt-ΔHBx-K3 refolding, the supernatant was treated with a reducing agent. Lane 6: After RAP1-mCD28$_{conv}$PEt-ΔHBx-K3 refolding, the supernatant was not treated with a reducing agent. Lane 7: After RAP1-mCD28$_{conv}$PEt-ΔHBx-K3 refolding, the precipitate was treated with a reducing agent. Lane 8: After RAP1-mCD28$_{conv}$PEt-ΔHBx-K3 refolding, the precipitate was not treated with a reducing agent.

Table 2 shows the results of quantitative analyses of the protein bands on the electrophoresis images of RAP1-mCD28$_{conv}$PEt-HBx$_{1-154}$-K3 and RAP1-mCD28$_{conv}$PEt-ΔHBx-K3 after protein refolding.

TABLE 2

| Target protein | Treatment | Lane | Image quantitative values |
|---|---|---|---|
| RAP1-mCD28$_{conv}$PEt-HBx$_{1-154}$-K3 | supernatant/with reducing agent | 1 | 410.92 |
| | supernatant/without reducing agent | 2 | 108.9 |
| | precipitate/with reducing agent | 3 | 17386.593 |
| | precipitate/without reducing agent | 4 | 17056.513 |
| RAP1-mCD28$_{conv}$PEt-ΔHBx-K3 | supernatant/with reducing agent | 5 | 3210.832 |
| | supernatant/without reducing agent | 6 | 956.648 |
| | precipitate/with reducing agent | 7 | 21631.815 |
| | precipitate/without reducing agent | 8 | 12612.48 |

Protein refolding comparisons were also made between RAP1-hCD28$_{conv}$PEt-HBx$_{1-154}$-K3 and RAP1-hCD28$_{conv}$PEt-ΔHBx-K3. Similar to the RAP1-mCD28$_{conv}$PEt-HBx$_{1-154}$-K3, the post-refolding recovery rate of the RAP1-hCD28$_{conv}$PEt-ΔHBx-K3 also increased by 10% as compared with RAP1-hCD28$_{conv}$PEt-HBx$_{1-154}$-K3 (data not shown). The result confirms that removal of HBx $21^{st}$-$50^{th}$ amino acids can reduce aggregation and improve recovery rate of the target protein.

Effectiveness of ΔHBx Fusion Protein as a Vaccine:
(1) Vaccine Immunogenicity Test:
Dosing schedule, methods, and animal groups:
C57BL/6 female mice (4-5 weeks old) were immunized once a week for 3 times via subcutaneous injections on Day 0, 7, 14, blood samples were collected on Day 0, 7, 14, 21, and serum anti-HBx specific antibodies were analyzed with ELISA. Mice were sacrificed and spleen collected. The immune cells in the spleen were stimulated with two HBx-specific peptide libraries (HBx small peptide pool-1, HBx small pool-2). The number of Th1-specific immune cells and secretion of cytokines species were analyzed with ELiSpot.

Figure 3:
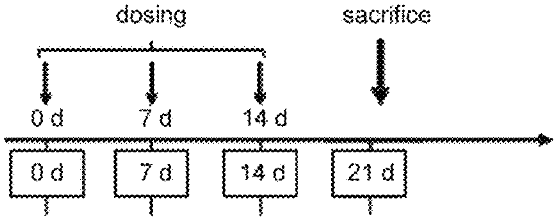
FIG. 3 shows immunization and sample collection schedules.

FIG. 3 shows schedules for three vaccinations given to C57BL/6 mice, and collections of blood and spleen samples. The animals were divided into two groups with 5 mice in each group. The control group was administered a PBS buffer, and the vaccine group was administered RAP1-mCD28$_{conv}$PEt-ΔHBx-K3+CpG ODN1826. Table 3 shows dosage given to each group and the animal numbers.

TABLE 3

| Experimental groups | Dose (mg) [antigen/adjuvant] | Number of animals |
|---|---|---|
| PBS Buffer (control group) | 0/0 | 5 |
| RAP1-mCD28$_{conv}$PEt-ΔHBx-K3 + CpG ODN1826 (vaccine group) | 0.1/0.02 | 5 |

Figure 4:
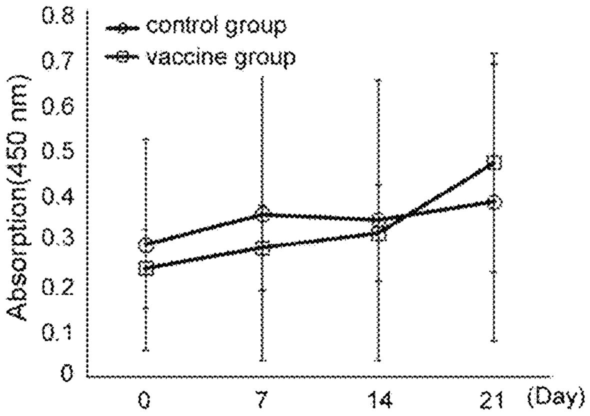
FIG. 4 is a chart showing the results of ELISA analysis of an antigen-specific humoral immune response elicited by the vaccine RAP1-mCD28$_{conv}$PEt-ΔHBx-K3+CpG ODN1826 in C57BL/6 mice. Purified recombinant HBx protein was used to capture serum HBx-specific antibody, and colors were displayed for comparing the absorbance of light penetration at a wavelength of 450 nm.

Results:
The C57BL/6 mice were immunized with RAP1-mCD28$_{conv}$PEt-ΔHBx-K3+CpG ODN1826. Serum samples collected on Day 0, 7, 14, 21 were analyzed for HBx-specific antibodies by ELISA (FIG. 4). The serum HBx-specific antibody levels on day 7 and day 14 in the vaccine group showed no significant changes, although showing a slight increase on Day 21, which was not statistically significant as compared with the control group. The results indicated that 3 times of immunizations with RAP1-mCD28$_{conv}$PEt-ΔHBx-K3+CpG ODN1826 did not induce a significant antigen-specific humoral immune response.

Figure 5:
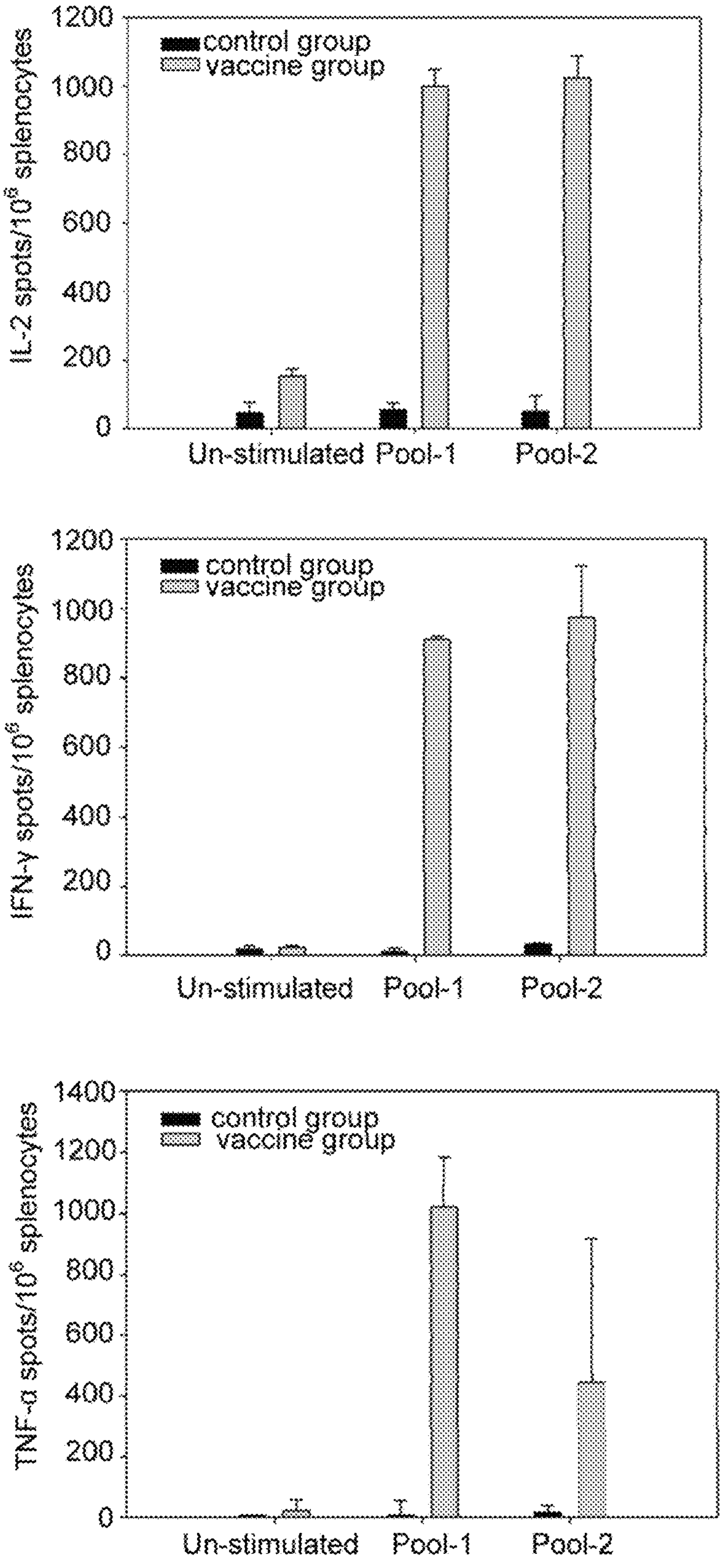
FIG. 5 shows a specific Th1 cell immune response induced by the vaccine RAP1-mCD28$_{conv}$PEt-ΔHBx-K3+CpG ODN1826 in C57BL/6 mice as analyzed by ELISPOT. The numbers of spleen immune cells that secreted IL-2 (top), IFNγ (middle), and TNFα (bottom) after stimulation by different HBx-specific peptide libraries (pool-1, pool-2) were compared.

The mice were sacrificed after 21 days. Their spleen immune cells were stimulated by two pools of different HBx-specific short peptides (HBx small peptide pool-1, HBx small peptide pool-2). A specific cell-mediated immunogenic response was analyzed by ELISPOT (ELISpot). There was a significant increase in the number of the mouse spleen immune cells that secreted IL-2 (top). IFNγ (middle) and TNFα (bottom) in the vaccine group (FIG. 5). In contrast, there was no increase in the number of the specific spleen immune cells that secreted IL-2, IFNγ, and TNFα in the mouse control group after stimulation with two different HBx-specific peptides.

In summary, FIGS. 4 and 5 indicate that vaccination with RAP1-mCD28$_{conv}$PEt-ΔHBx-K3+CpG ODN1826 subcutaneously once a week for three times could effectively elicit HBx-specific Th1 cell-mediated immune response, although it could not induce HBx-specific humoral immune response in the vaccinated C57BL/6 mice.

(2) Vaccine Therapeutic Efficacy Test

Animal Experimental Model:

Male mice of a CBA line (5-6 weeks old) were used to establish an animal model carrying a long-term hepatitis B virus (HBV carrier mice). A mixture of pAAV/HBV1.2 plasmid and saline (in the amount of about 8% of the equivalent weight of mice) was intravenously injected into the tail vein of mice at a high pressure (hydrodynamic injection, HDI) in a fast mode (5-10 seconds), which forced the plasmid to penetrate the cell membrane and enter liver cells. The liver cells carrying the plasmid express hepatitis B virus proteins. Virus can assemble inside the liver cells and release therefrom. A surface antigen (HBsAg) is also released into blood. This animal model emulates a human patient afflicted with chronic hepatitis B symptoms.

Figure 6:
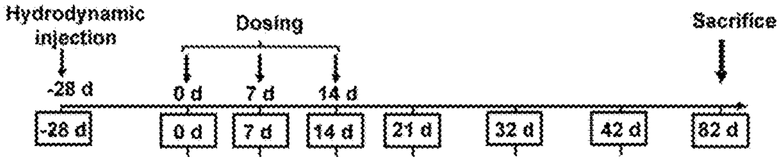
FIG. 6 shows establishment of hepatitis B virus (HBV) carrier mouse model, sampling process, and a dosing schedule.

Dosing schedule, methods, and animal groups:

Twenty eight days after the high-pressure injection, the CBA mice were treated with the therapeutic vaccine on Day 0, Day 7, Day 14, via subcutaneous injections once a week for three times (FIG. 6). The body weights were measured on the same day of high-pressure injection, Day 0, Day 7, Day 14, Day 21, Day 32, and Day 42. Blood was collected for analyses of alanine aminotransferase (ALT), bilirubin, viral DNA, and surface antigen (HBsAg). Mice were sacrificed 82 days after the first vaccination, and liver core antigen (HBcAg) quantity was analyzed by western blotting.

Mice were divided into 3 experimental groups as follows: The control group was administered with PBS buffer, the adjuvant group was administered with CpG ODN1826; and the vaccine group was administered with RAP1-mCD28$_{conv}$PEt-ΔHBx-K3+CpG ODN1826. Table 4 shows the animal groups, dosage, and the number of animals in each group.

TABLE 4

| dosing groups | dosage (mg) [antigen/adjuvant] | number of animals |
|---|---|---|
| PBS buffer (control group) | 0/0 | 7 |
| CpG ODN1826 (adjuvant group) | 0/0.02 | 10 |
| RAP1-mCD28$_{conv}$PEt-ΔHBx-K3 + CpG ODN1826 (vaccine group) | 0.1/0.02 | 10 |

Figure 7:
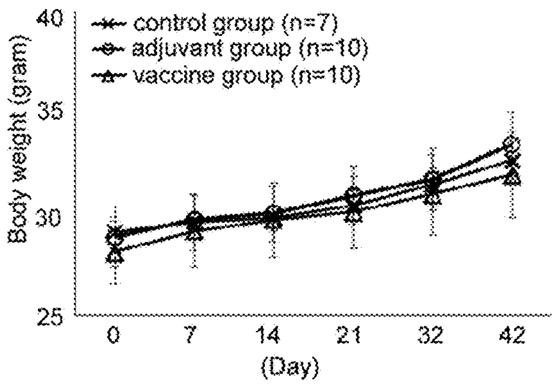
FIG. 7. shows body weight changes in the HBV carrier mice after vaccination.
Figure 8:
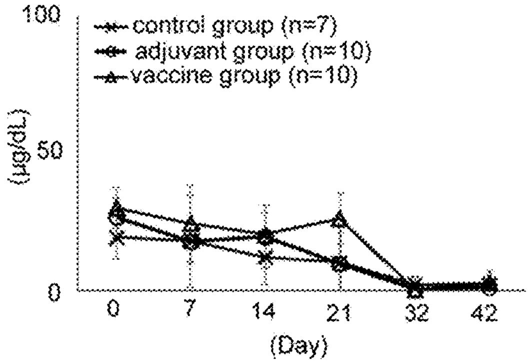
FIG. 8 shows total bilirubin changes in the HBV carrier mice after vaccination.
Figure 9:
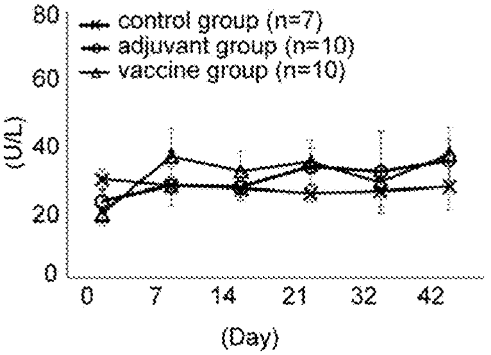
FIG. 9 is a chart showing changes in serum alanine aminotransferase (ALT) values in the HBV carrier mice after vaccination.

Results:

The body weight (FIG. 7) and total bilirubin (FIG. 8) did not show abnormal changes in the vaccine group, and showed no significant difference from the control and adjuvant groups. This indicates that the vaccine exhibited a high tolerance in the HBV carrier mice. The serum alanine aminotransferase (ALT) level was slightly higher, and showed significant fluctuations over time in the vaccine group (FIG. 9). Eight out of 10 mice in the vaccine group had the serum ALT levels above the normal range (40 U/L or less), but their serum ALT levels returned to the normal value on the subsequent blood sampling points.

As to the adjuvant group, the serum ALT level also increased slightly, and showed slight fluctuations. However, the average value did not exceeded the normal range. The serum ALT level in the control group was normal, and had no significant fluctuations. The results indicate that the vaccine and adjuvant, when used in the HBV carrier mice, are likely to induce a specific immune response, clear infected liver cells, lead to mild liver inflammation, and result in an increase and fluctuations in the serum ALT level.

Figure 10:
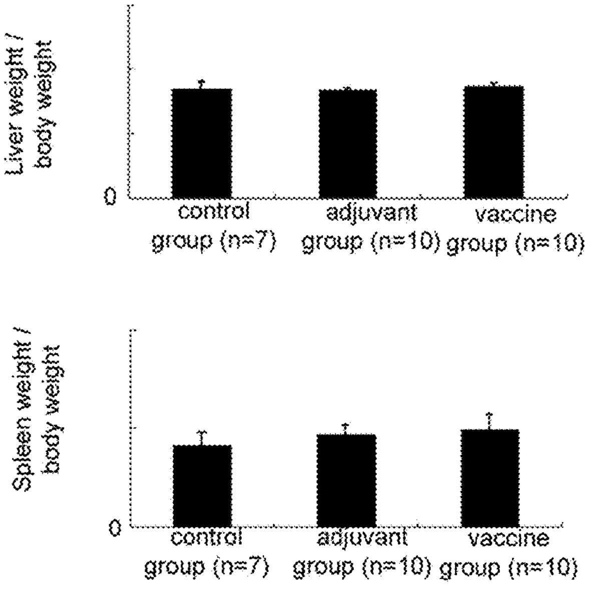
FIG. 10 shows liver (top) and spleen (bottom) weight ratios in the HBV carrier mice on Day-82 after the first vaccination.

Mice were sacrificed 82 days after the first dosing. The weight ratios of liver and spleen versus body weight were measured (FIG. 10 top and bottom, respectively). There was no difference in the liver weight ratio among the three groups, indicating that the adjuvant and vaccine had no obvious effects on the liver. However, the spleen weight ratio in the adjuvant group was slightly higher than the control group, and the spleen weight ratio in the vaccine group was further slightly higher than the adjuvant group. Although the differences were not statistically significant, but this might indicate that an immune response was elicited by the adjuvant and vaccine and resulted in a slight increase in the spleen weight ratio.

The changes in the viral markers (i.e. HBV DNA and HBsAg) in the serum samples showed a significant difference among the experimental groups. The average value of the serum viral DNA load in the control group maintained at 40,000-120,000 copies/ml with a positive rate of 100% up to 42 days (FIG. 11, top and bottom), which indicates that an HBV carrier CBA mouse model (HBV carrier mice) was successfully established. The positive rate in each group was calculated as follows: the number of animals with a serum viral DNA load of greater than 1000 copies/ml (limit of detection, LOD) divided by the total number of the animals.

Figure 11:
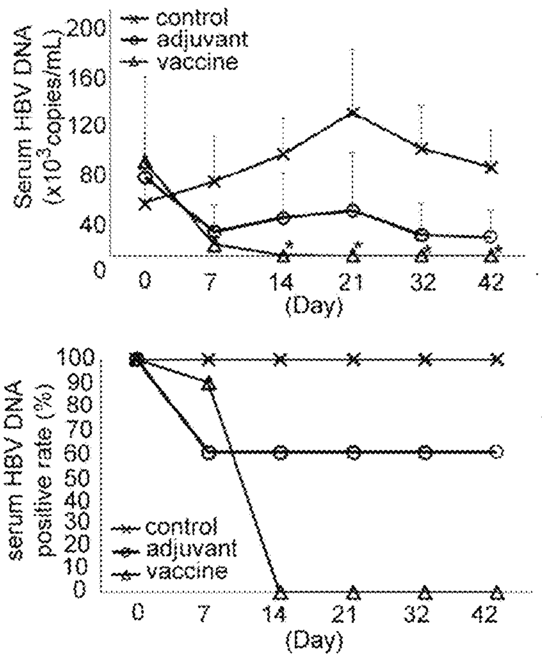
FIG. 11 shows changes of the serum viral DNA load (×1000 copies/ml) (top) DNA and the positive rate (>1000 copies/ml) (bottom) in the HBV carrier mice after vaccination. A statistically significant difference ($P<0.05$) between the adjuvant and vaccine group is indicated by*. The number of mice in each group was as follows: control group (n=7), adjuvant group (n=10), vaccine group (n=10).

The average value of the viral DNA load in the adjuvant group decreased from about 80,000 copies/ml on day 0 to about 15,000 copies/ml on Day 7 (7 days after the first dose administration) with a positive rate being decrease to 60% (FIG. 11, bottom). The average value of the viral DNA load after the second and third dose administrations did not show further changes significantly, maintaining stable and sustainable through Day 42.

In contrast, the average value of the viral DNA load in the vaccine group started at the level of about 80.000 copies/ml on day 0, and dramatically reduced on Day 7 (7 days after the first dose administration), although still with a positive rate of 90% (FIG. 1, bottom). The viral DNA was no longer detectable on Day 14 (7 days after the second dose) in all mice of the vaccine group, showing a statistically significant difference from the adjuvant group (FIG. 11, top). The viral DNA maintained undetectable up to 42 days (FIG. 11, bottom).

Figure 12:
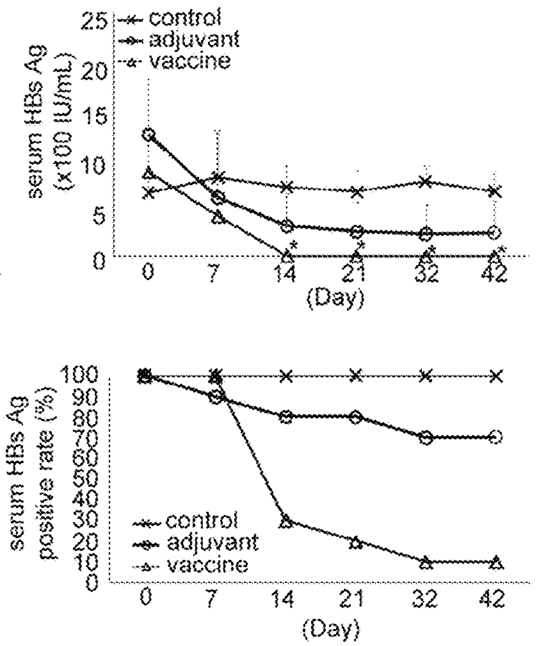
FIG. 12 shows the changes of the serum surface antigen number (×100 IU/ml) (top) and the positive rate (>0.05 IU/ml) (bottom) in the HBV carrier mice after vaccination. A statistically significant difference ($P<0.05$) between the adjuvant and vaccine group is indicated by *.

The average value of the surface antigens and the changes in the positive rate showed a positive correlation with the serum viral DNA load. The control group showed that the serum surface antigen (HBsAg) level remained stable at 600-800 IU/ml with a positive rate of 100% all the way through the 42nd days (FIG. 12, top and bottom). The positive rate in each group was calculated as follows: the number of animals with a serum surface antigen level of greater than 0.05 IU/ml divided by the total number of the animals.

The adjuvant group showed that the average value of the serum surface antigen (HBsAg) level was about 1200 IU/ml on day 0, reduced to about 500 IU/ml on Day 7 (7 days after the first dose administration), and about 400 IU/ml on Day 14 (7 days after the second dose), with no further significant decline after the third dose administration (FIG. 12, top). Thereafter, the serum surface antigen level maintained at the same value through the 42nd day. The surface antigen positive rate in the adjuvant group fell to 90% on Day 7, to 80% on Day 14, and to 70% on Day-32, showing a slow downward trend (FIG. 12, bottom).

The vaccine group showed that the average value of the serum surface antigen (HBsAg) on day 0 was about 800 IU/ml. It plummeted to about 2 IU/ml on Day 14 (7 days after the second dose) and further dropped to less than 1 IU/mL on Day 21, Day 32 and Day 42. There was a statistically significant difference in the serum surface antigen level between the vaccine group and the adjuvant group, and this difference was stable and continued all the way through the 42nd day (FIG. 12, top). The surface antigen positive rate in the vaccine group declined substantially to 30% on Day 14 (7 days after the second dose), and further dropped to 20% and 10% on Day 21 and Day 32, respectively (FIG. 12, bottom).

The results indicate that administration of the vaccine RAP1-mCD28$_{conv}$PEt-ΔHBx-K3+CpG ODN1826 could induce an HBx-specific immune response, cleared the infected liver cells, suppressed viral replication inside the mouse body, and also almost stopped the production and release of the surface antigen. The effect of the vaccine on the HBV carrier mice might be partly from the antiviral effect of the adjuvant, or from the synergism of the vaccine and the adjuvant, which enhanced the anti-viral effect.

Figure 13:
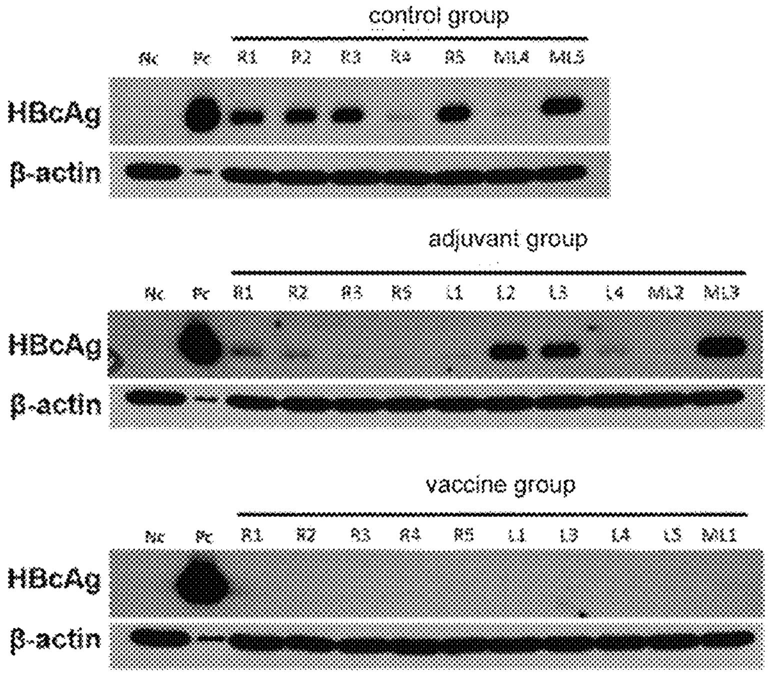
FIG. 13 are photographs showing the results of western blot analysis of liver core antigen expression in the HBV carrier mice 82 days after the first vaccination.

Western blot was used to compare the amount of the core antigen (HBcAg) expression in the liver tissue between the animal groups 82 days after the first vaccination. The core antigen expression was detected in all the liver tissues obtained from the control group, in which 5 mice showed a higher amount of HBcAg expression, and 2 mice (R4, MIA) showed less expression (FIG. 13, top). The core antigen expression in the adjuvant group was high in three mice (L2, L3, ML3), moderate in 3 other mice (R1, R2, L4), and weak in 4 other mice (R3, R5, L1, ML2) (FIG. 13, middle). In contrast, the core antigen expression in the vaccine group was weak or not detectable in almost all the liver tissues from the vaccine group (FIG. 13, Bottom).

The western blot results were in consistency with the immunohistochemical staining results (data not shown), and were positively correlated with the serum viral DNA load and virus surface antigen positive rate (FIG. 11, bottom and FIG. 12, bottom). This indicate that after the vaccinations, the liver cells that expressed viral antigens might have been destroyed by the immune system, or the viral antigen expression might have been suppressed.

A core antibody specific against HBcAg was used to detect the core antigen (HBcAg) in the liver tissues, and the core antigen (HBcAg) expression in the mouse liver was quantified and compared among the control, adjuvant, and vaccine groups (FIG. 13, top, middle, and bottom, respectively). β-actin: internal control; Nc: negative control (blank, CBA mouse liver cells); Pc: positive control (HepG2.2.15 cell line).

Other ΔHBx Fusion Proteins

Using a similar design as disclosed above, the following ΔHBx fusion proteins are generated: (1) RAP1-CD28$_{conv}$PEt-ΔHBx (2) PE$_{1-252}$-CD28$_{conv}$PEt-ΔHBx; (3) A2M Minimum-CD28$_{conv}$PEt-ΔHBx; (4) HIV-Tat Minimum-CD28$_{conv}$PEt-ΔHBx; (5) HSPs Minimum-CD28$_{conv}$PEt-ΔHBx; (6) PE$_{1-252}$-CD28$_{conv}$PEt-ΔHBx-K3; (7) A2M Minimum-CD28$_{conv}$PEt-ΔHBx-K3; (8) HIV-Tat Minimum-CD28$_{conv}$PEt-ΔHBx-K3; (9) HSPs Minimum-CD28$_{conv}$PEt-ΔHBx-K3.

The immunogenicity of these ΔHBx fusion proteins are tested using similar experimental designs, dosing and sampling schedules described above and in FIGS. 3 and 6. It is expectable that these fusion proteins would enter antigen-presenting cells (APCs) through their own APC-binding domain or CD91 receptor-binding domain. The epitope of the antigen ΔHBx would be presented to the membrane surface of APCs, leading to induction of a hepatitis B virus X protein (HBx)-specific T cell response. Therefore, these fusion proteins are also effective in inhibiting the proliferation of hepatitis B virus in liver cells and/or suppressing hepatitis B virus infection in HBV patients. The fusion proteins according to the invention have the same mechanism of action as the fusion proteins disclosed in U.S. Pat. No. 9,481,714.

The foregoing description of the exemplary embodiments of the invention has been presented only for the purposes of illustration and description and is not intended to be exhaustive or to limit the invention to the precise forms disclosed. Many modifications and variations are possible in light of the above teaching.

Alternative embodiments will become apparent to those skilled in the art to which the present invention pertains without departing from its spirit and scope. Accordingly, the scope of the present invention is defined by the appended claims rather than the foregoing description and the exemplary embodiments described therein. Some references, which may include patents, patent applications and various publications, are cited and discussed in the description of this invention. All references cited and discussed in this specification are incorporated herein by reference in their entireties and to the same extent as if each reference was individually incorporated by reference.

What is claimed is:

1. A fusion protein comprising:

(a) an antigen-presenting cell (APC)-binding domain or a CD91 receptor-binding domain, located at the N-terminus of the fusion protein;

(b) a protein transduction domain, located at the C-terminus of the APC-binding domain or the CD91 receptor-binding domain, wherein the protein transduction domain is a fusion polypeptide comprising:

(1) a T cell sensitizing signal-transducing peptide consisting of 28-53 amino acid residues in length, comprising the amino acid sequence of SEQ ID NO: 28, in which $Xaa^8$ is I or L; $Xaa^{10}$ is V, F or A, $Xaa^{11}$ is M or L, $Xaa^{17}$ is L or I, being located at the N-terminus of the fusion polypeptide;

(2) a translocation peptide consisting of 34-112 amino acid residues in length, comprising an amino acid sequence that is at least 90% identical to SEQ ID NO: 3, 4, 20 or 30; and (3) a linker linking the T cell sensitizing signal-transducing peptide and the translocation peptide; and (c) an antigen comprising a hepatitis B virus X protein deletion mutant (AlHBx) that lacks residues at least from amino acid residue 21 to amino acid residue 50, located at the C-terminus of the protein transduction domain.

2. The fusion protein of claim 1, wherein the APC-binding domain or the CD91 receptor-binding domain comprises an amino acid sequence that is at least 90% identical to the sequence selected from the group consisting of SEQ ID NOs: 5, 9, 6, 7, and 8.

3. The fusion protein of claim 1, further comprising an endoplasmic reticulum retention sequence located at the C-terminus of the fusion protein.

4. The fusion protein of claim 1, wherein the fusion protein is free of an endoplasmic reticulum retention sequence at C-terminus thereof if the antigen contains 10 or more epitopes.

5. The fusion protein of claim 1, wherein the protein transduction domain comprises the amino acid sequence of SEQ ID NO: 27.

6. The fusion protein of claim 1, wherein the APC-binding domain or the CD91 receptor-binding domain comprises an amino acid sequence selected from the group consisting of SEQ ID NOs: 5, 9, 6, 7, and 8.

7. The fusion protein of claim 1, wherein the T cell sensitizing signal-transducing peptide comprises an amino acid sequence selected from the group consisting of SEQ ID NO: 1 and 2.

8. The fusion protein of claim 1, wherein the translocation peptide comprises the amino acid sequence of SEQ ID NO: 3.

9. The fusion protein of claim 1, wherein the antigen comprises the amino acid sequence of SEQ ID NO: 23.

10. The fusion protein of claim 1, wherein the deletion mutant ΔHBx has a deletion of amino acids (aa) 1 to 50, or as 5 to 50, or aa 10 to 50, or aa 15 to 50, or aa 18 to 50.

11. A vaccine composition comprising:

(a) a therapeutically effective amount of the fusion protein of claim 1; and (b) an adjuvant.

12. The vaccine composition of claim 11, wherein the adjuvant comprises CpG oligodeoxynucleotide.

13. A method for inducing a hepatitis B virus X protein (HBx)-specific T cell response, comprising:

administering a therapeutically effective amount of the fusion protein of claim 1 to a subject in need thereof.

14. A method for treating infection caused by hepatitis B virus, and/or minimizing symptoms caused by hepatitis B virus infection, comprising:

administering a therapeutically effective amount of the fusion protein of claim 1 to a subject in need thereof.

15. A method of inhibiting proliferation of hepatitis B virus in liver cells and/or suppressing hepatitis B virus infection in a subject in need thereof, comprising:

administering a therapeutically effective amount of the fusion protein of claim 1 to the subject in need thereof.

16. A method for preparation of a hepatitis B virus X protein deletion mutant fusion protein, comprising:

(a) generating a plasmid for expressing the fusion protein of claim 1;

(b) causing the plasmid to express the fusion protein within a host cell; and (c) collecting the fusion protein from the host cell.

17. The fusion protein of claim 1, wherein the deletion mutant ΔHBx has a deletion of 30 amino acid residues from as 21 to aa 50.

18. The fusion protein of claim 17, wherein the translocation peptide comprises the amino acid sequence of SEQ ID NO: 3.

19. The fusion protein of claim 18, further comprising an endoplasmic reticulum retention sequence located at the C-terminus of the fusion protein.

20. The fusion protein of claim 1, wherein the protein transduction domain comprises the amino acid sequence of SEQ ID NO: 22.

* * * * *